United States Patent [19]
Botich et al.

[11] Patent Number: 6,123,688
[45] Date of Patent: Sep. 26, 2000

[54] PRE-FILLED RETRACTABLE NEEDLE INJECTION DEVICES

[75] Inventors: Michael J. Botich, Oxnard; Thor R. Halseth, Simi Valley, both of Calif.

[73] Assignee: MDC Investment Holdings, Inc., Wilmington, Del.

[21] Appl. No.: 08/922,905

[22] Filed: Sep. 3, 1997

Related U.S. Application Data

[63] Continuation-in-part of application No. 08/699,998, Aug. 20, 1996, Pat. No. 5,788,677.
[60] Provisional application No. 60/002,630, Aug. 22, 1995, provisional application No. 60/004,450, Sep. 29, 1995, and provisional application No. 60/005,895, Oct. 26, 1995.

[51] Int. Cl.[7] .................................................. A61M 5/315
[52] U.S. Cl. ........................ 604/220; 604/195; 604/187; 604/201; 604/110; 604/203
[58] Field of Search .................................... 604/195, 187, 604/221, 196, 201, 231, 110, 203, 192, 193, 200, 218, 205, 91, 232, 198, 220, 181

[56] References Cited

U.S. PATENT DOCUMENTS

| | | | |
|---|---|---|---|
| 2,562,129 | 7/1951 | Scherer et al. | 128/215 |
| 2,778,360 | 1/1957 | Miskel | 128/218 |
| 3,739,780 | 6/1973 | Ogle | 128/220 |
| 3,766,919 | 10/1973 | Cloyd | 128/220 |
| 3,916,894 | 11/1975 | Cloyd | 128/220 |
| 3,989,044 | 11/1976 | Meierhoefer | 128/218 N |
| 4,078,565 | 3/1978 | Genese | 128/220 |
| 4,764,413 | 8/1988 | Haber et al. . | |
| 4,808,169 | 2/1989 | Haber et al. . | |
| 4,820,275 | 4/1989 | Haber et al. . | |
| 4,826,489 | 5/1989 | Haber et al. . | |
| 4,834,717 | 5/1989 | Haber et al. . | |
| 4,838,863 | 6/1989 | Allard et al. . | |
| 4,838,869 | 6/1989 | Allard . | |
| 4,874,382 | 10/1989 | Lindemann et al. . | |
| 4,900,307 | 2/1990 | Kulli . | |

(List continued on next page.)

*Primary Examiner*—Corrine McDermott
*Assistant Examiner*—Cris L. Rodiguez
*Attorney, Agent, or Firm*—Dann, Dorfman, Herrell and Skillman; Stephen H. Eland

[57] ABSTRACT

A pre-filled injection device having a retractable needle with a sharpened tip for penetrating the skin of a patient for administering medicinal fluids is provided. The pre-filled injection device of the present invention allows the needle to be manually retracted, thereby reducing the risk of transmission of various pathogens, most notably human immune virus (HIV), to infected personnel, due to an inadvertent needle stick. The present pre-filled injection device has a hollow housing which receives a pre-filled cartridge containing medicinal fluids. A needle retainer initially holds a needle projecting forwardly from the hollow housing. The rear end of the needle pierces the pre-filled cartridge when sufficient pressure is applied to the end of the pre-filled cartridge to advance it in the forward direction. A plunger is slidably displaceable within the housing. A latch member is operable in a latched position to prevent forward movement of the plunger. The latch member is operable in an unlatched position to permit forward movement of the plunger and retract the needle into the hollow housing.

20 Claims, 16 Drawing Sheets

U.S. PATENT DOCUMENTS

| | | |
|---|---|---|
| 4,909,794 | 3/1990 | Haber et al. . |
| 4,919,657 | 4/1990 | Haber et al. . |
| 4,927,414 | 5/1990 | Kulli . |
| 4,931,040 | 6/1990 | Haber et al. . |
| 4,936,830 | 6/1990 | Verlier . |
| 4,966,593 | 10/1990 | Lennox . |
| 4,994,034 | 2/1991 | Botich et al. . |
| 5,019,052 | 5/1991 | Rohrbough ............................ 604/203 |
| 5,049,133 | 9/1991 | Pascual . |
| 5,098,382 | 3/1992 | Haber et al. . |
| 5,112,307 | 5/1992 | Haber et al. . |
| 5,114,404 | 5/1992 | Paxton et al. . |
| 5,129,884 | 7/1992 | Dysarz . |
| 5,180,369 | 1/1993 | Dysarz . |
| 5,188,599 | 2/1993 | Botich et al. . |
| 5,207,647 | 5/1993 | Phelps . |
| 5,261,880 | 11/1993 | Streck et al. . |
| 5,263,942 | 11/1993 | Smedley et al. . |
| 5,269,760 | 12/1993 | Bina ......................................... 604/110 |
| 5,330,430 | 7/1994 | Sullivan . |
| 5,338,311 | 8/1994 | Mahurkar . |
| 5,358,491 | 10/1994 | Johnson et al. . |
| 5,385,551 | 1/1995 | Shaw ....................................... 604/110 |
| 5,399,170 | 3/1995 | Whitley . |
| 5,407,431 | 4/1995 | Botich et al. . |
| 5,458,580 | 10/1995 | Hajishorch . |
| 5,478,324 | 12/1995 | Meyer ..................................... 604/203 |
| 5,520,642 | 5/1996 | Bigagli et al. ........................... 604/88 |
| 5,527,285 | 6/1996 | Lenz et al. . |
| 5,634,903 | 6/1997 | Kurose et al. .......................... 604/110 |
| 5,637,903 | 6/1997 | Kurose et al. . |
| 5,685,863 | 11/1997 | Botich et al. ........................... 604/198 |
| 5,800,395 | 9/1998 | Botich et al. ........................... 604/110 |
| 5,997,512 | 12/1999 | Shaw ....................................... 604/195 |
| 6,004,278 | 12/1999 | Botich et al. ........................... 600/576 |
| 6,010,486 | 1/2000 | Carter et al. ............................ 604/195 |
| 6,015,438 | 1/2000 | Shaw ....................................... 624/195 |

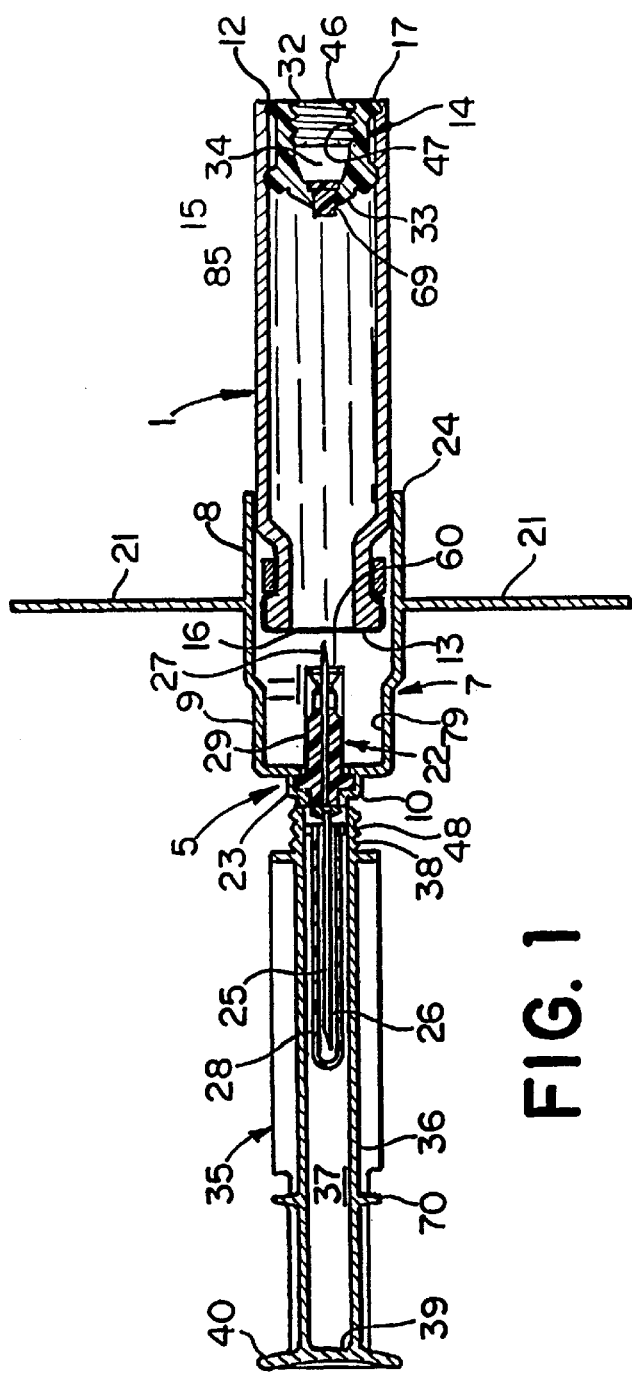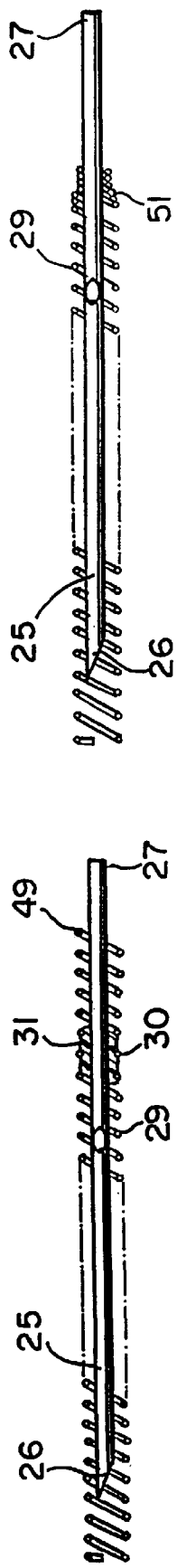
FIG. 1
FIG. 2A
FIG. 2B

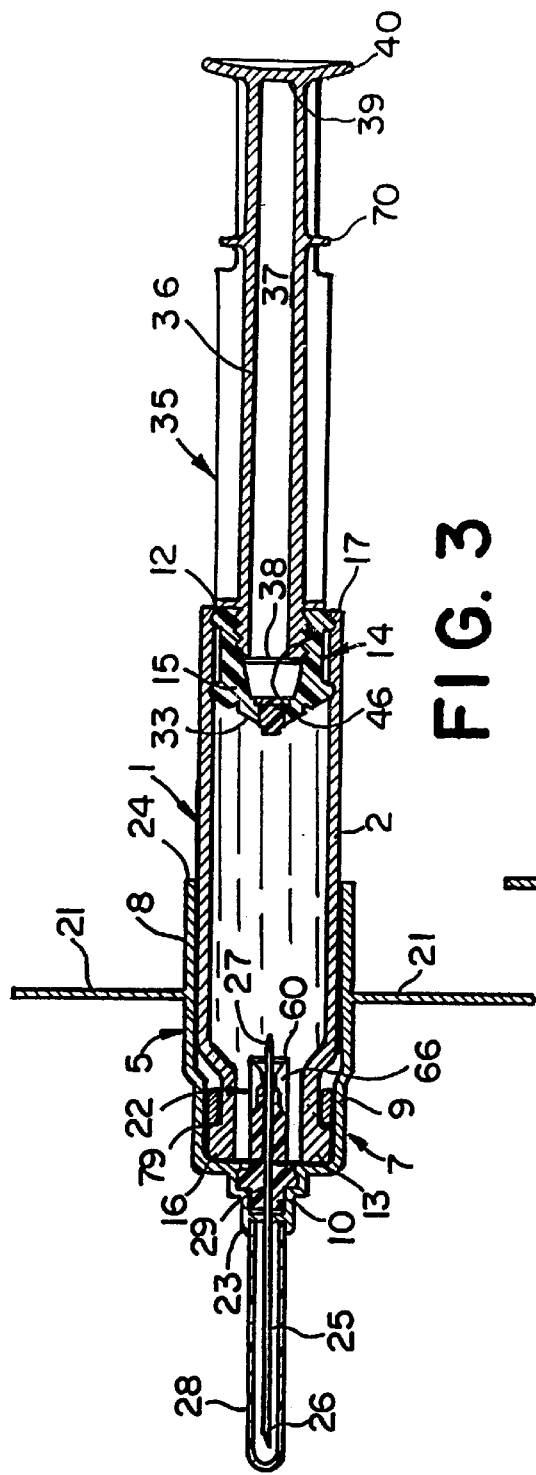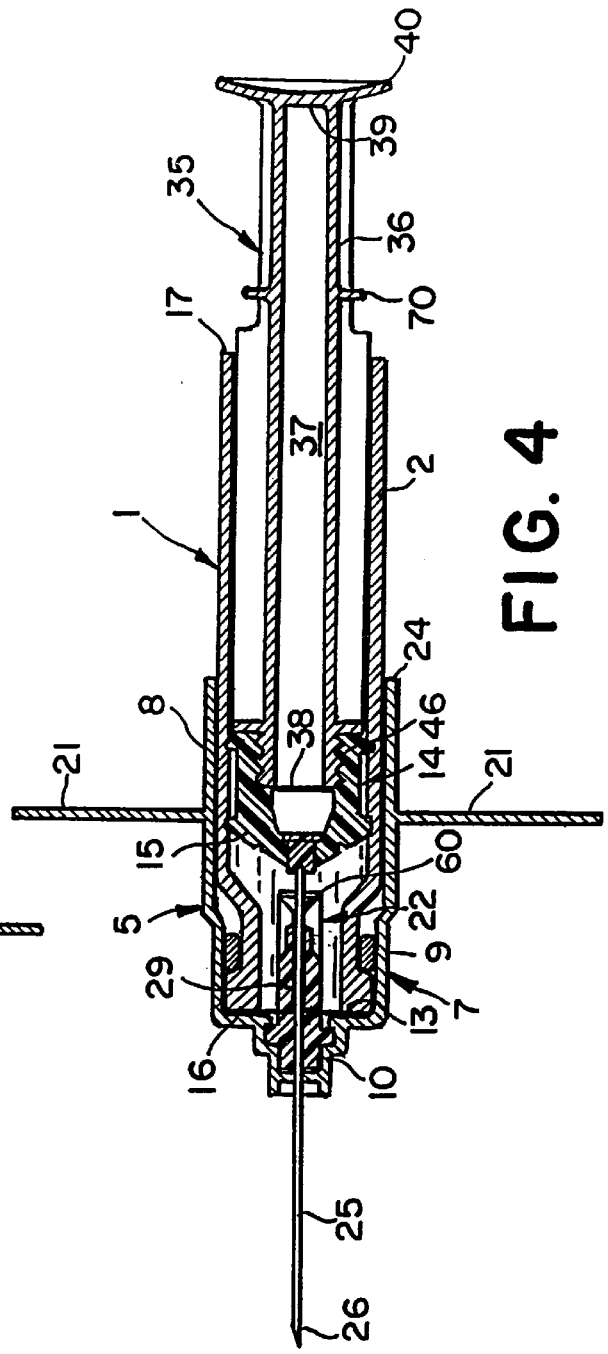

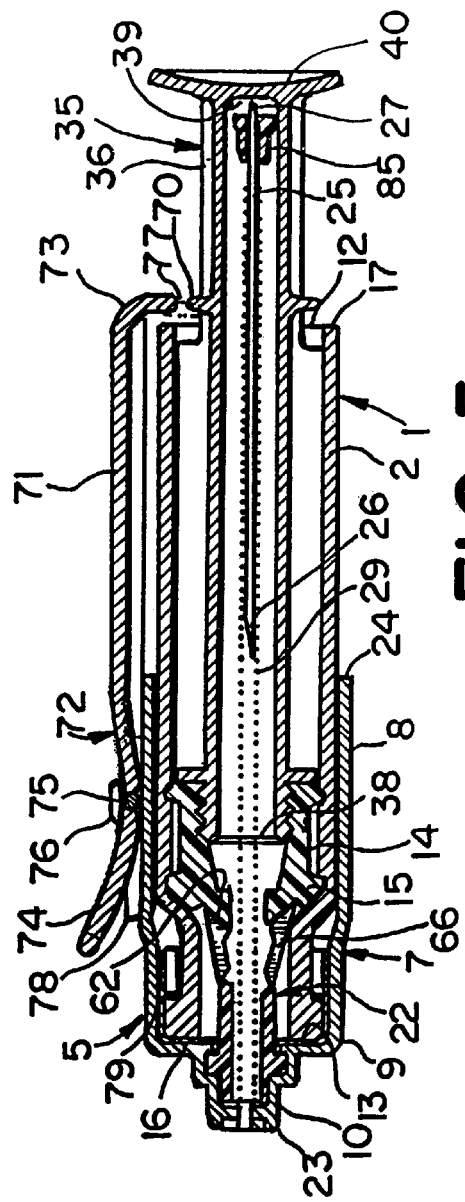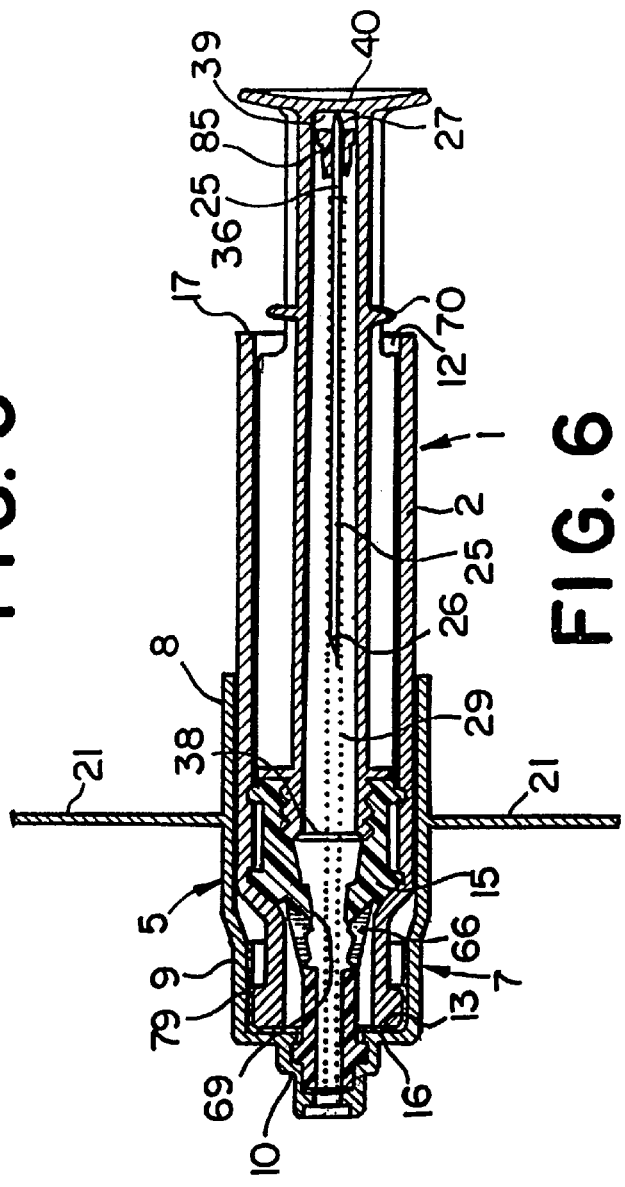

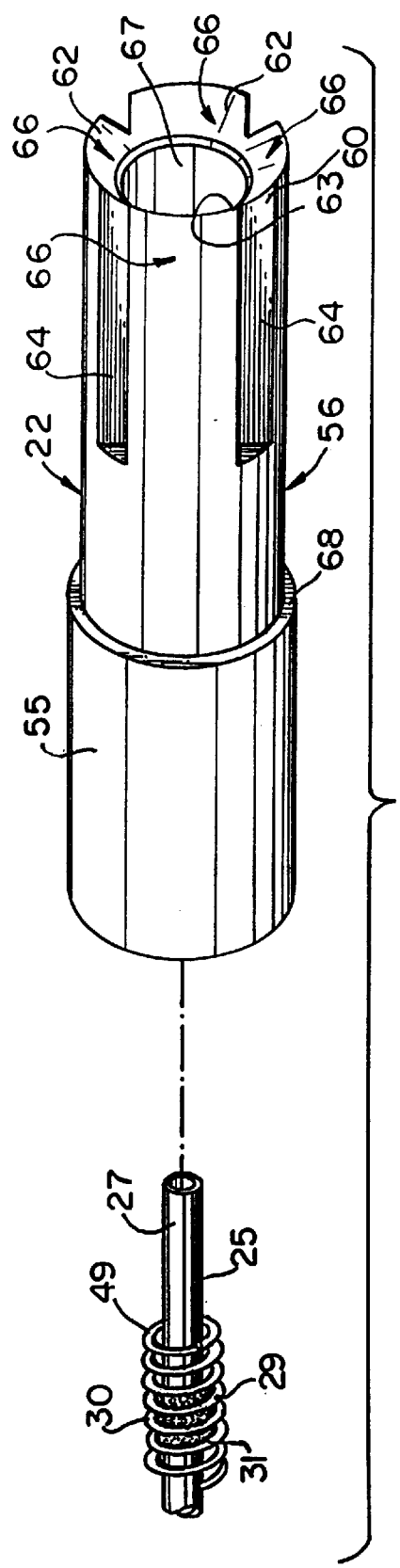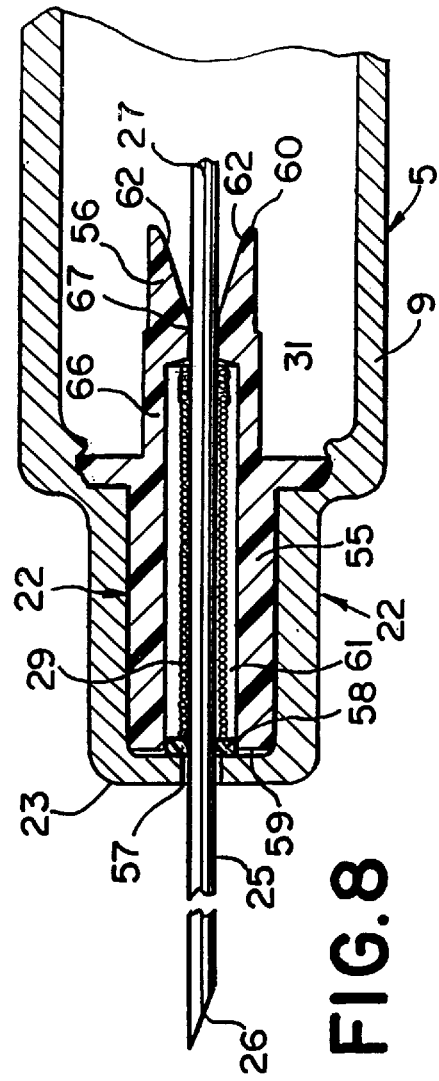
FIG. 7
FIG. 8

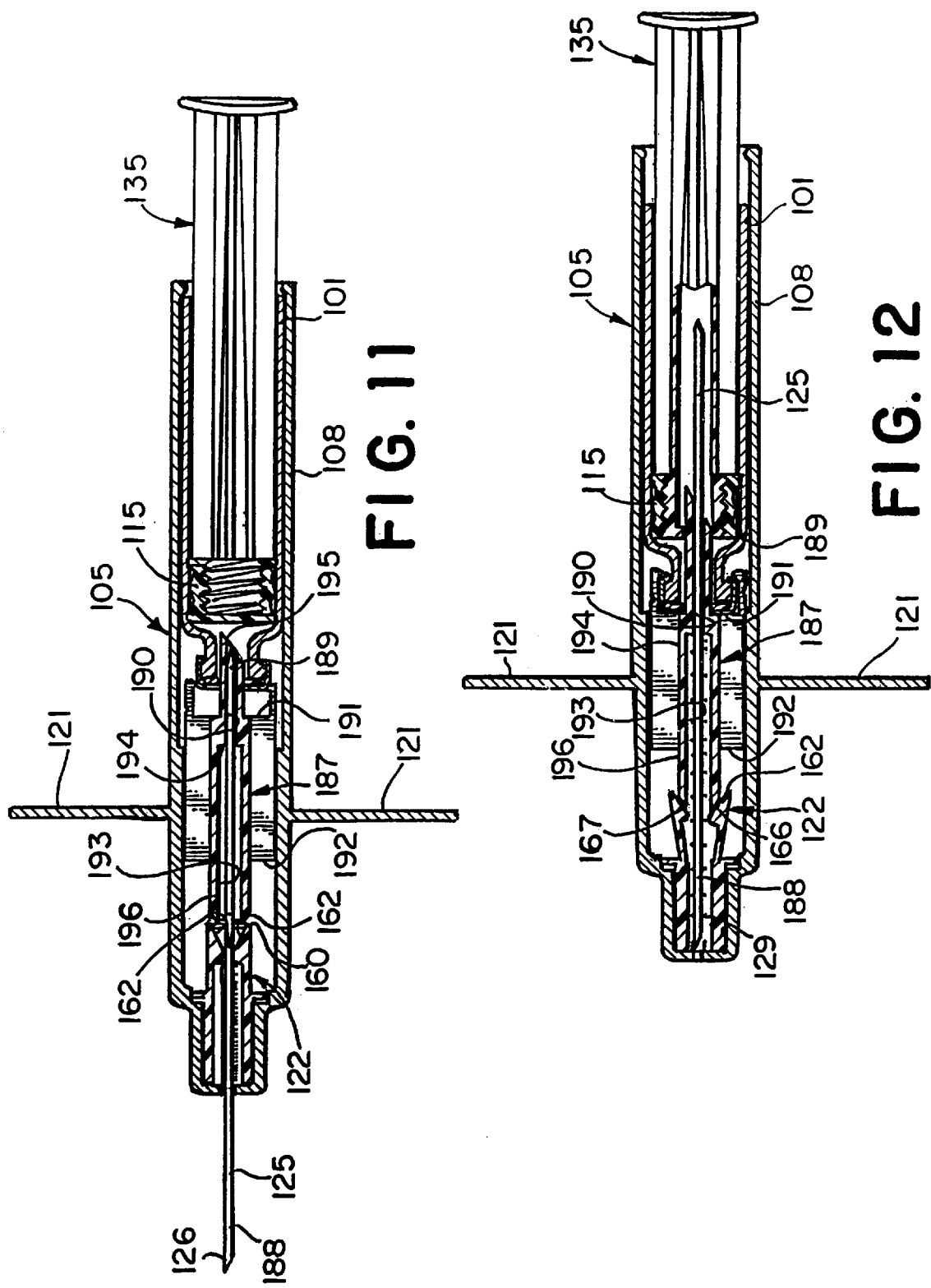

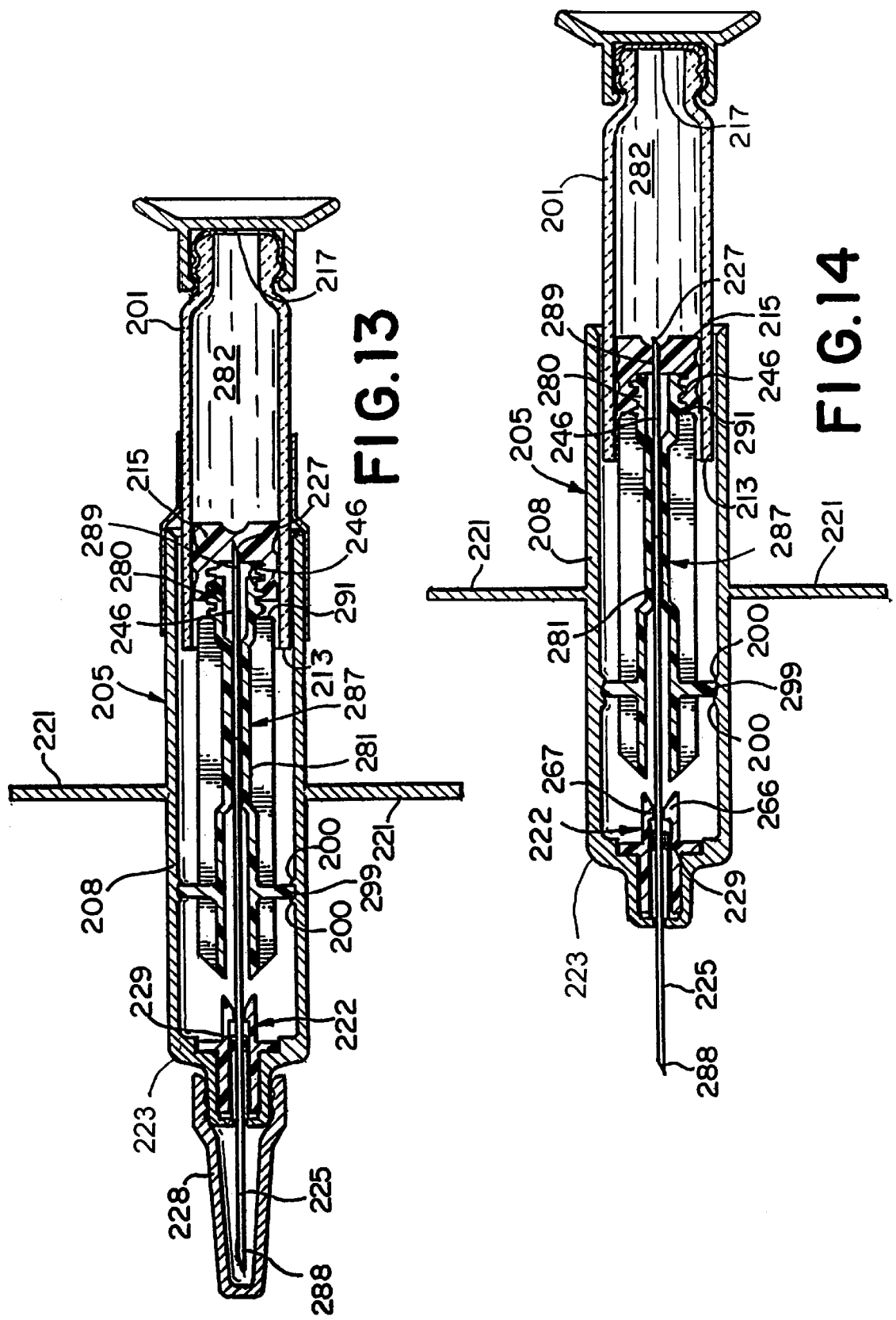

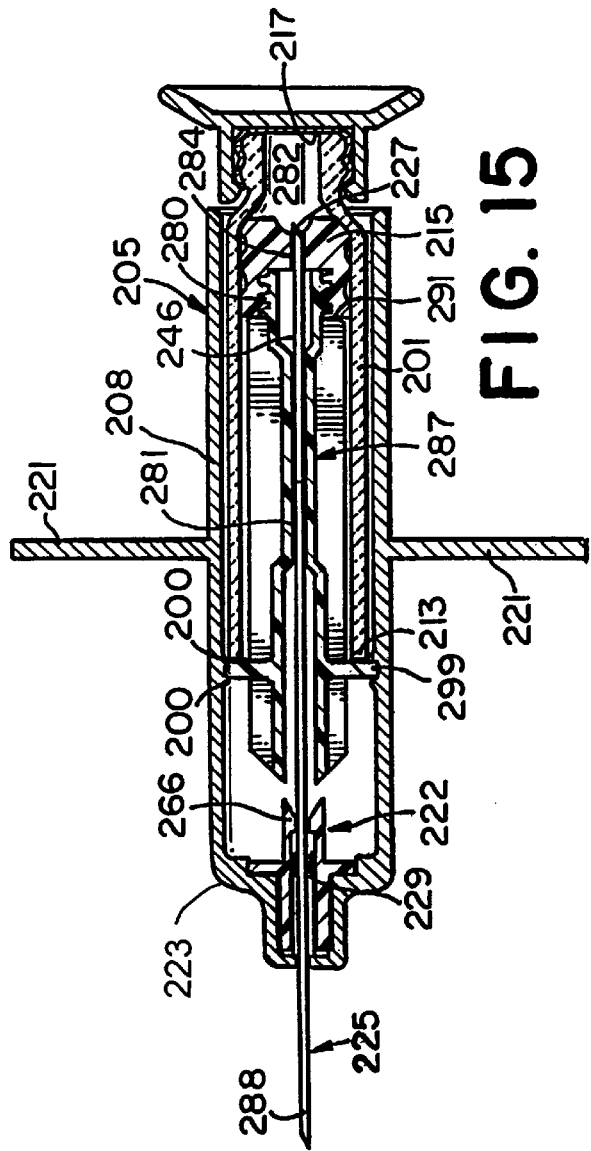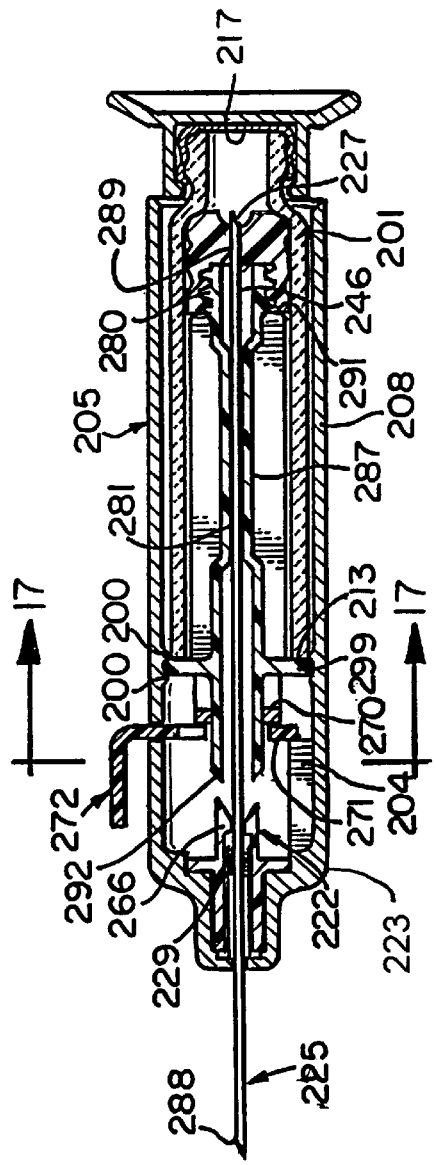

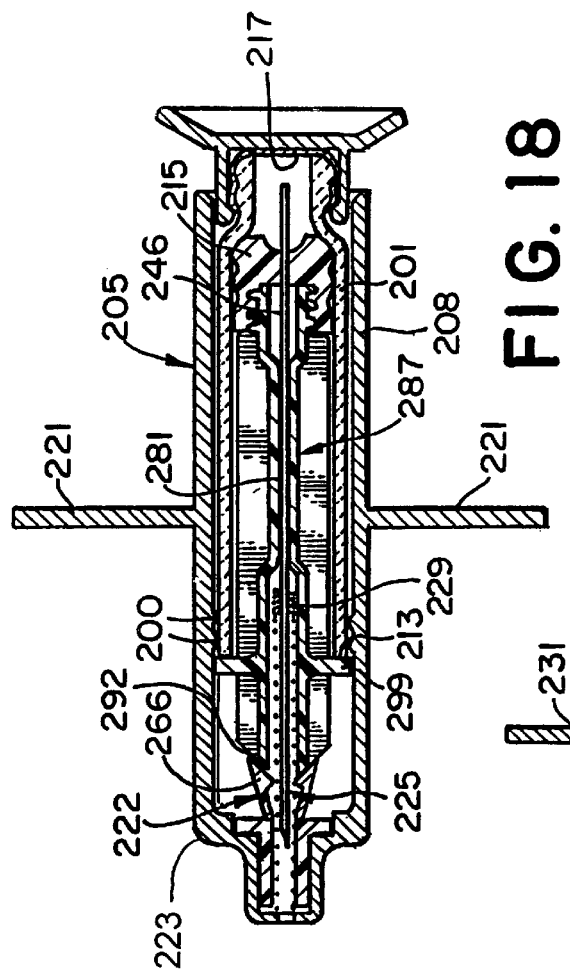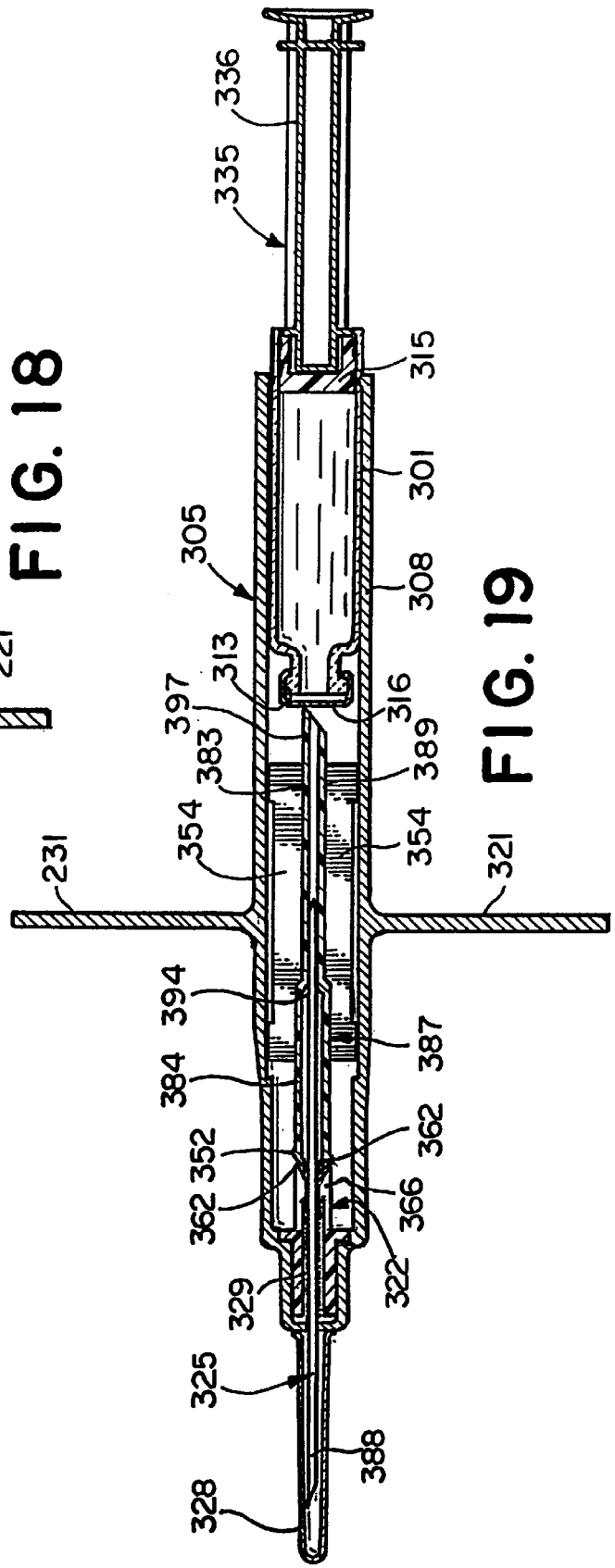

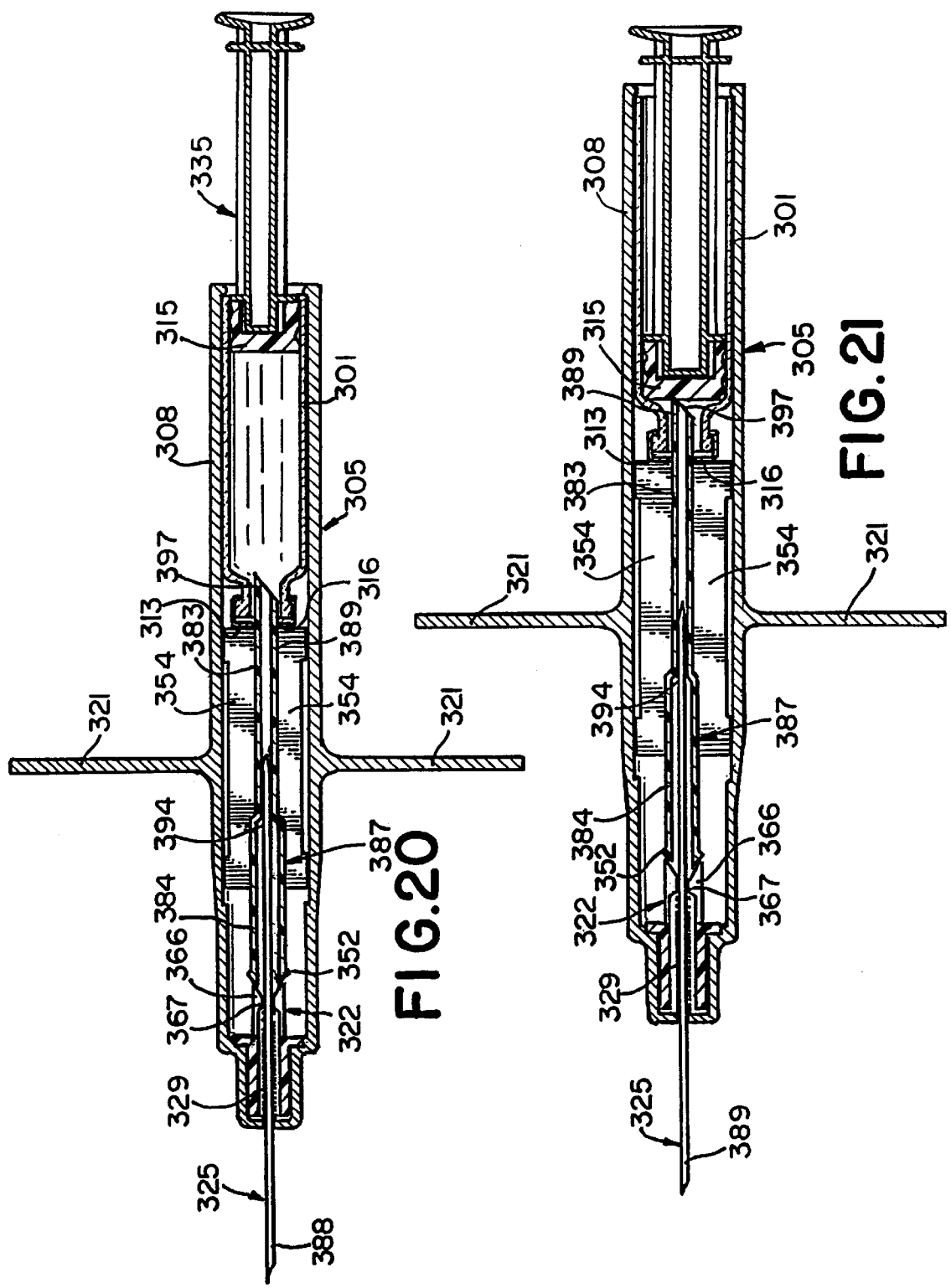

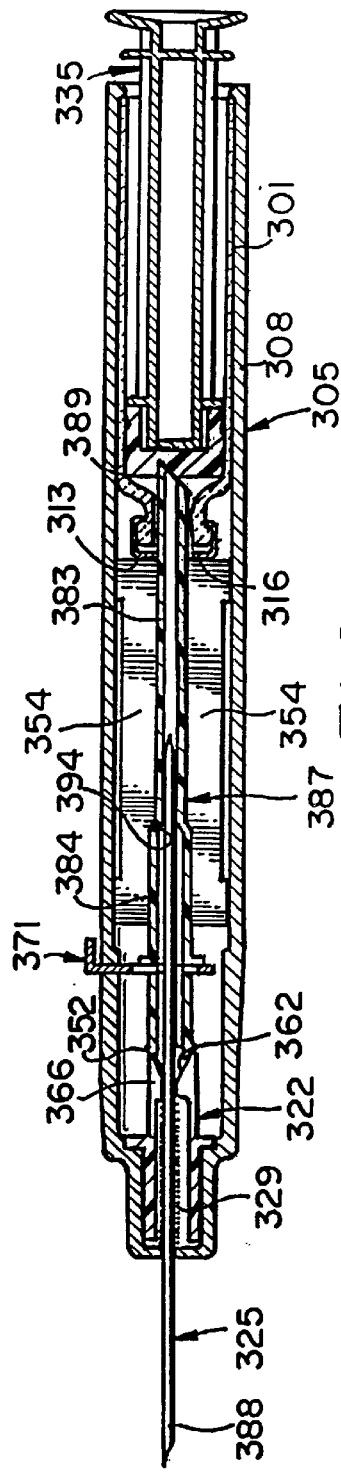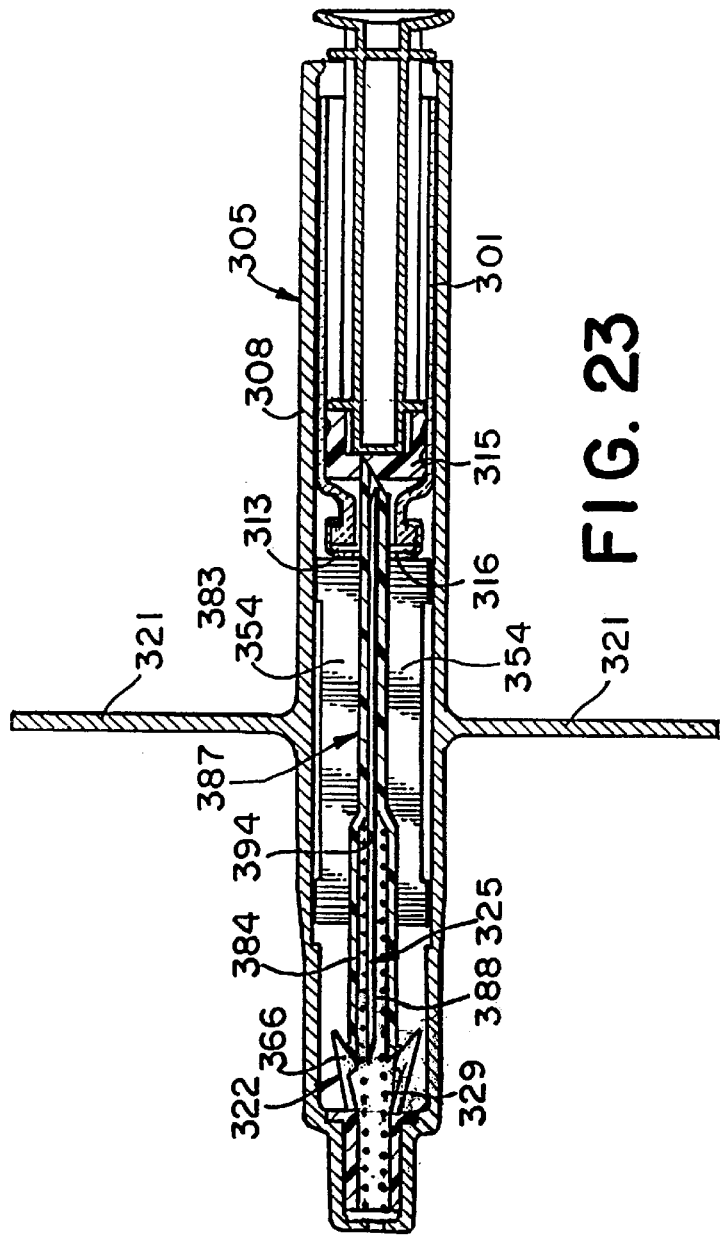

PRE-FILLED RETRACTABLE NEEDLE INJECTION DEVICES

CROSS-REFERENCE TO RELATED APPLICATIONS

This is a continuation-in-part of U.S. patent application Ser. No. 08/699,998, filed Aug. 20, 1996, now U.S. Pat. No. 5,788,677, in which priority is claimed to each of U.S. Provisional Application No. 06/002,630, filed Aug. 22, 1995; U.S. Provisional Application No. 60/004,450, filed Sep. 29, 1995; and Provisional Application No. 60/005,895, filed Oct. 26, 1995. Priority under 35 U.S.C. §119(e) is claimed herein to U.S. Provisional Application No. 60/025,342, filed Sep. 3, 1996 and U.S. Provisional Application No. 60/050,797, filed Jun. 26, 1997.

Each of the aforementioned applications is hereby incorporated herein by reference.

FIELD OF THE INVENTION

The present invention relates to pre-filled ampoules, carpules, or cartridges for administering injections of medicinal fluids to patients. More specifically, the invention relates to such devices having a retractable needle feature for rendering them non-reusable and safely disposable.

BRIEF DESCRIPTION OF THE DRAWINGS

FIG. 1 is a cross-sectional view of an ampoule and ampoule housing apparatus according to a first embodiment of the invention and showing the apparatus in an as-shipped condition;

FIG. 2A is an exploded view of a needle and spring in which the spring is shown attached to the needle using adhesive or epoxy;

FIG. 2B is an exploded view of a needle and spring in which the spring is shown attached to the needle by crimping the spring to the needle;

FIG. 3 is a cross-sectional view of the ampoule and ampoule apparatus of FIG. 1 shown assembled prior to injection of fluid;

FIG. 4 is a cross-sectional view of the ampoule and ampoule apparatus of FIG. 1 showing the ampoule and plunger after the medication has been expelled;

FIG. 5 is a cross-sectional view of the ampoule and ampoule apparatus of FIG. 1 showing a lever lock for preventing premature retraction of the needle and showing the lever in alternative locked and unlocked positions;

FIG. 6 is a cross-sectional view of the ampoule and ampoule apparatus of FIG. 1 showing the condition of the apparatus after retraction of the needle;

FIG. 7 is an exploded perspective view of a spring needle and needle retainer with parts of the needle and spring broken away;

FIG. 8 is an enlarged cross-sectional view of the needle, spring and needle retainer of FIG. 7 and showing the needle and spring in place within the needle retainer and showing part of the ampoule housing broken away;

FIG. 11 is a cross-sectional view of the ampoule and ampoule apparatus of FIG. 9 showing the condition of the apparatus after the medication has been expelled from the ampoule;

FIG. 12 is a cross-sectional view of the ampoule and ampoule apparatus of FIG. 9 showing the condition of the apparatus after retraction of the needle;

FIG. 13 is a cross-sectional view of an ampoule and an ampoule housing apparatus according to a third embodiment of the invention, and showing the apparatus in an as-shipped condition;

FIG. 14 is a cross-sectional view of the ampoule and ampoule apparatus of FIG. 13 assembled prior to injection of fluid;

FIG. 15 is a cross-sectional view of the ampoule and ampoule apparatus of FIG. 13 showing the condition of the apparatus after the medication has been expelled from the ampoule;

FIG. 16 is a cross-sectional, side view of the ampoule and ampoule apparatus of FIG. 13 showing a latching mechanism for the apparatus for preventing premature retraction;

FIG. 18 is a further cross-sectional view of the ampoule and ampoule apparatus showing the needle retracted into the apparatus;

FIG. 19 is a cross-sectional view of an ampoule and an ampoule housing apparatus, according to a fourth embodiment of the invention, showing the apparatus in an as-shipped condition;

FIG. 20 is a cross-sectional view of the ampoule and ampoule apparatus of FIG. 19 showing its condition prior to use;

FIG. 21 is a cross-sectional view of the ampoule and ampoule apparatus of FIG. 19 showing the condition of the apparatus after the medication has been expelled from the ampoule;

FIG. 22 is a cross-sectional view of the ampoule and ampoule apparatus of FIG. 21 showing a latch mechanism on the apparatus for preventing premature retraction and with the lock in its locked position;

FIG. 23 is a cross-sectional view of the ampoule and ampoule apparatus of FIG. 19 showing the needle retracted into the apparatus;

DETAILED DESCRIPTION

Figure 9:
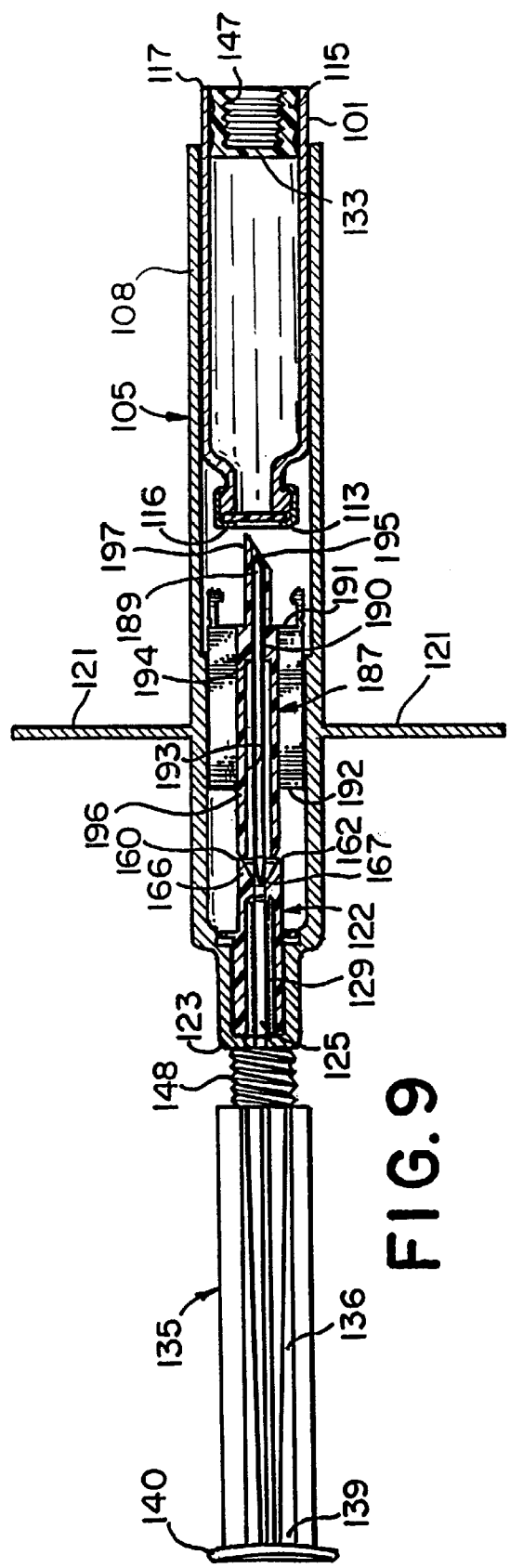
FIG. 9 is a cross-sectional view of an ampoule and ampoule housing apparatus according to a second embodiment of the invention, showing the apparatus in an as-shipped condition.

Referring now to FIGS. 1–6, there is shown a first embodiment of a pre-filled injection ampoule 1 and an ampoule apparatus 5. The ampoule apparatus 5 has a main body or housing 7, which comprises a tubular barrel 8, a reduced diameter tubular forward portion 9, and a further reduced diameter nose portion 10. The interior of the barrel 8 defines a chamber 11 for receiving the ampoule 1. A piston assembly 14 with piston 15 is slidably positioned at the back end 17 of the ampoule 1. The piston assembly 14 is disposed within the walls of the ampoule 1 forming a seal to prevent the fluid from leaking out of the ampoule 1 through its rear opening 12. To further guard against leakage of fluid from the ampoule 1, an annular groove may be formed about the forward end of the piston 15 for retaining a sealing member.

A volume of medicinal fluid, preferably in an amount sufficient for a single dose of the fluid or in an amount preferred for administration to a single patient, is contained within the ampoule 1 between the piston 15 and the forward end 13 of the ampoule 1.

Figure 24:
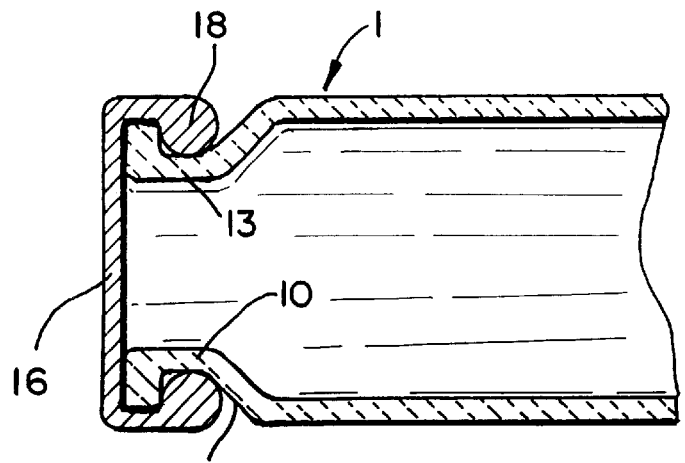
FIG. 24 is a cross-sectional view of the forward end of an ampoule in accordance with the present invention.
Figure 25:
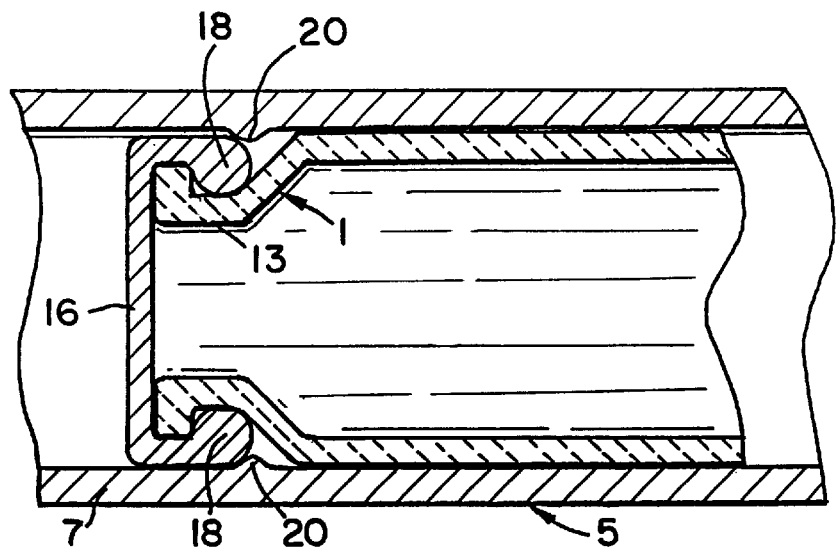
FIG. 25 is a cross-sectional view of a detent formed within the interior of an ampoule housing for retaining an ampoule within the ampoule housing in accordance with the present invention.

The forward end 13 of ampoule 1 is sealed by a puncturable membrane 16 which is preferably made of an elastomeric material. The membrane 16 is attached to cover the front 13 of the ampoule 1. As shown in FIG. 24, the membrane 16 may be held in position by an annular sealing ring 18 that is engaged within a circumferential groove 19 formed about the outside of the forward end 13 of the ampoule 1. The sealing ring 18 may be an O-ring that is integrally formed with the membrane 16. Alternatively, the sealing ring 18 may be a separate semi-rigid structure for compressively holding the membrane 16 to the forward end 13 of the ampoule 1. As shown in FIG. 25, a detent 20 is formed within the interior of the housing 7 for receiving the periphery of the sealing member 18 when in place about the forward end 13 of the ampoule 1, and for retaining the ampoule 1 within the ampoule apparatus 5 in the assembled configuration prior to use.

Referring to FIG. 1, external projections, such as finger grips 21, are formed along the exterior of the ampoule apparatus 5 to allow the user to more easily maneuver the ampoule 1 and ampoule housing 7.

A needle retainer 22 is positioned within the forward portion 23 of the ampoule apparatus 5 for retaining a needle 25 projecting from the apparatus 5, as shown in FIGS. 1, 2 and 8. The needle 25 is preferably made of stainless steel for chemical compatibility with various medications. The forward portion 26 of the needle 25 is preferably surrounded by a cap or sheath 28 that is removably attached in a connectional manner to the exterior of the forward portion 23 of the ampoule apparatus 5, as indicated in FIG. 1. The rear portion 27 of the needle 25 extends generally axially into the apparatus 5 and projects rearwardly beyond the needle retainer 22. The needle retainer 22 is held within the forward portion 23 of the ampoule apparatus 5, as by a press fit or as by glue. A spring 29 surrounds the needle 26 within the needle retainer 22 and has a rearward portion 30 fixed to the needle 26, as shown in FIG. 24 and explained more fully hereinafter.

A plunger member 35 is provided for connection to the rear end 32 of the piston 15, as shown in FIG. 3. The plunger 35 is manually depressed for moving the piston 15 to expel medication from the ampoule 1. In the embodiment shown in FIG. 1, the plunger member 35 is shaped to nest over the exposed needle 25 and its protective sheath 28. The plunger member 35 can be detachably coupled to the forward end 23 of the ampoule apparatus 5 over the needle 25 and its protective sheath 28 for ease of shipment, as shown in FIG. 1. The plunger member 35 comprises a plunger rod 36 having an axial channel or cavity 37. The cavity 37 is appropriately sized to receive the needle 25 and its protective sheath 28 therein. Further, when the plunger rod 36 is coupled to the piston 15, as shown in FIGS. 3–6, the cavity 37 is adapted to receive the needle 25 when the needle 25 is retracted, as shown in FIG. 6. The rear end 39 of the plunger rod 36 includes a broadened actuating surface 40 upon which force is applied by a user for urging the plunger rod 36 in the forward direction during injection of fluid from the ampoule 1.

Figure 26:
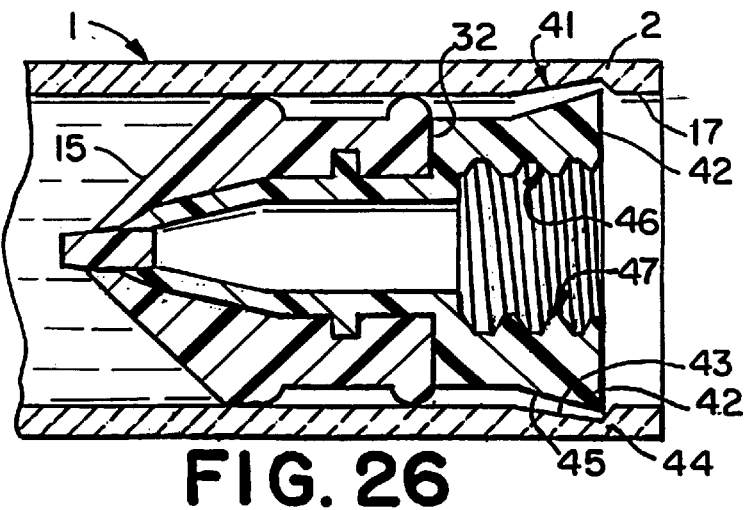
FIG. 26 is a fragmentary cross-sectional view of a piston assembly in accordance with the present invention, in which the dotted line represents a center line of the piston.

As shown in FIG. 26, the piston 15 and the ampoule 1 preferably include cooperating surfaces for positioning and retaining the piston 15 at the rear 17 of the ampoule 1. For this purpose, an annular cavity 41 may be formed circumferentially about the inside surface of the ampoule 1 for being engaged by one or more tabs 42 projecting radially from the exterior of the piston 15. The cavity 41 preferably has an obliquely angled rear surface 43 and a more nearly perpendicular forward surface 44. The tabs 42 have complementary angled surfaces 45 to permit the piston 15 to be inserted into the barrel 2 and fixed in position during assembly of the ampoule 1 but prevent the piston from being withdrawn from the back of the ampoule. A removable rear cap may also be provided to cover the rear 17 of the ampoule 1 prior to use, in order to prevent the rear 32 of the piston 15 from being accidentally or inadvertently depressed during transportation, storage, or other handling of the ampoule 1.

The rear portion 32 of the piston 15 includes a receptacle 46 for receiving the forward end 38 of the plunger rod 36. As shown in FIG. 1, the receptacle 46 comprises a bore which is sized to mate with and hold the forward portion 38 of the plunger rod 36, as shown, for example, in FIG. 3.

Alternatively, as shown in FIG. 26, the receptacle 46 may comprise a threaded interface 47. In this arrangement, a tip member 48 attached to the forward end 38 of the plunger rod 36 is provided for mating with the receptacle 46 of piston 15, and is preferably threaded for engagement with the threaded surface 47 of the receptacle 46.

The ampoule 1 is preferably transparent and may have graduations thereon for indicating the volume of fluid contained therein. Prior to administering the medicinal fluid to a patient, the user may expel an initial volume of fluid from the ampoule 1 in order to obtain a desired, smaller dose of the fluid for delivery to the patient.

The ampoule 1 is preferably formed of a material that is chemically compatible with the fluid medication in the ampoule 1. For storage of some medications, polypropylene is a suitable inert material. For storage of some other types of medications, glass may be preferred for the ampoule 1.

The cap 28 is held upon the forward portion 23 of the housing 7 by, for example, cooperative engagement between a lateral protrusion formed upon the exterior of the forward portion 23 of the housing 7 and an annular mating recess formed within the rear of the cap 28.

A plug member can optionally be located or formed within the sheath 28 for receiving and sealing the tip 26 of needle 25 during shipment. The plug member is preferably held in the interior of the cap 28, so that when the cap 28 is removed from the housing 7 to expose the needle 25 immediately prior to administering an injection, the plug member is likewise removed from the tip 26 of the needle 25. The plug member may be formed within the cap 28 during assembly thereof by depositing a quantity of a silicone elastomer, or other suitable material. As the cap is positioned upon the housing 7, the needle 25 penetrates the plug member to be sealed thereby.

As shown in FIG. 2A, the spring 29 is preferably attached to needle 25 using adhesive or epoxy 31. When attaching the spring 29 to the needle 25 using adhesive or epoxy 31, it is preferred to use an ultraviolet (UV) curable adhesive, such as Loctite 3001, which is distributed by LOCTITE. For ease of manufacture, the spring 29 is bonded to the needle 25 at a location 30 spaced from the rear end 49 of the spring 29, as indicated in FIG. 2A, so that one or more coils of the spring 29 can be grasped during the bonding process to insure that the spring 29 and needle 25 are properly oriented.

Alternatively, as shown in FIG. 2B, the spring 29 may be attached to the needle 25 by crimping the spring 29 to the needle 25 at a reduced diameter portion 51 of the spring 29. In this arrangement, the reduced diameter portion 51 of the spring 29 may also be bonded to the needle 25 to assure the coupling of the parts together.

As best shown in FIGS. 7 and 8, the needle retainer assembly 22 includes a front alignment portion 55 and a rear needle retainer mechanism 56. The front alignment portion 55 of the needle retainer 22 has a needle guideway 57 formed in the forward portion thereof, through which the needle 25 extends in the projecting configuration, as shown in FIG. 8. The needle guideway 57 is sized for maintaining the needle 25 in axial alignment in the apparatus 5. A sealing member 58, such as a resilient cup, washer, silicone plug, or puncturable disc, may be disposed at the front inside diameter of the front alignment portion 55. The sealing member 58 is compressed and surrounds the needle 25. The sealing member 58 further promotes axial alignment of the needle 25, and also serves to prevent fluid from passing through the needle guideway 57 subsequent to retraction of the needle 25 by expanding to seal the guideway 57.

The front alignment portion 55 of the needle retainer 22 is firmly engaged within the forward portion 23 of the ampoule housing 7, as by friction. The attachment of the alignment portion 55 of the needle retainer 22 within the forward portion 23 of the housing 7 may be further secured by epoxy or ultrasonic welding. Other effective means for securing the alignment portion 55 within the forward portion 23 of the housing 7 will be apparent to those skilled in the art.

The tubular needle retainer 22 is formed in two portions and retains the spring 29 and needle 25, as shown in FIG. 8. The forward end 59 of the needle retainer 22 holds the spring 29 and has a forward opening 57 to align the needle 25, as previously explained. The rear portion 60 of the needle retainer 22 includes the retainer mechanism 56, the operation of which is explained more fully hereinafter.

Referring to FIG. 5, the plunger 35 further includes an annular flange 70 which forms a stop. The flange 70 mates with a latch stop member 71 having a latch stop 77 at the rear end 73 of a lever lock 72. The annular flange 70 is positioned at a point along the length of the plunger 35 to permit the plunger 35 to be pushed through the barrel 2 to completely expel the medication within the ampoule 1 before the flange 70 abuts the lever lock 72. More specifically, the lever lock 72 comprises a latch member 71 which is pivotally connected to the outside of the housing 7 at pivot pin 75 held between side members fixed 76 to the housing 7. The latch member 71 on one side extends parallel along the outside of the housing 7 and is curved inwardly at the end of the housing to terminate in latch stop 77, which is adapted to abut the flange 70 of the plunger 35. On the other side of the pivot pin 75, the latch member extends toward the front end 23 of the ampoule apparatus 5 but is curved outwardly from the housing 7 to pivot the latch member 71 about the pivot pin 75. A tab 78 is cut out of the latch member and is bent downwardly to rest on the housing 7 to bias the latch member 71 to firmly engage the latch stop 77 with the flange 70, thereby restricting forward motion of the plunger 35 into the apparatus 5. The latch stop 77 is disengaged from the flange 70 by pressing on the forward end 74 of the latch member 71, thereby pivoting the latch stop 77 of the latch member 71 away from the flange 70, as shown in the alternative showing of the latch member (dotted lines) in FIG. 5. With the latch stop 77 disengaged from the flange 70, the plunger 35 can be further advanced in the forward direction to cause needle retraction.

The operation of the ampoule 1 and ampoule housing apparatus 5 will now be described. Referring to FIG. 1, in order to administer the medicinal fluid to a patient, the forward end 13 of ampoule 1 is inserted into the rear 24 of ampoule apparatus 5. The ampoule 1 is advanced within the barrel 8 until the rear end 27 of needle 25 abuts, but does not puncture, the membrane 16 which seals the forward end 13 of the ampoule 1. To prevent the ampoule 1 from advancement into the housing 5 beyond the desired initial position, a first detent formed along the inner surface of the barrel 8 of the ampoule housing 5 may be provided to inhibit the ampoule 1 from being advanced passed the desired point. To prepare the apparatus 5 for injecting the medication, the ampoule 1 is then advanced in the forward direction within the barrel 8 of the ampoule housing 5, by applying sufficient pressure to the rear end 17 of the ampoule 1 to advance the ampoule 1 passed the first detent so that the rear end 27 of the needle 25 punctures the membrane 16. A second detent 79 is formed along the inner surface of the barrel 8 of the ampoule housing 5 to inhibit the ampoule 1 from being advanced passed the second detent 79. The plunger member 35 is then detached from the forward end 23 of the ampoule housing 5 and secured to the piston 15 at the rear 17 of the ampoule 1. The cap 28 is then removed to expose the needle 25. The user may t en administer the medicinal fluid to a patient by penetrating the skin of the patient with needle 25 and then urging the plunger 35 in the forward direction to cause the piston 15 to expel the medicinal fluid from the ampoule 1 and through the needle 25 into the patient. Alternatively, the needle 25 may be used to penetrate an injection port of an intravenous access device connected with the patient for administration of a so-called "IV push". The plunger rod 36 is advanced within the barrel 8 until the latch member 71 engages the flange 70 formed in the plunger 35. In this position of the plunger 35, the piston 15 abuts against the rear end 60 of the needle retainer 22.

After the fluid has been administered to the patient, the needle 25 is removed from the patient, or from the injection port. The user presses on the forward end 74 of the latch member 72 to disengage the latch member 71 from the flange 70 formed on the plunger 35 to permit the plunger 35 to be further advanced. A firm compressive force, preferably in excess of the force required to expel fluid during an injection stroke, is then applied to the rear 39 of the plunger rod 36. The force also advances the piston 15 forward against the rear end 27 of the needle 25 to break a frangible end member 85 of the piston 15, as explained more fully hereinafter. A retraction mechanism responsive to such compressive force, which is described hereinbelow, then causes the needle 25 to be withdrawn into the cavity 37 within the plunger 35, so that the needle 25 no longer presents a sharp injury hazard. The plunger 35, the ampoule 1, and the ampoule housing 5 may then safely be discarded.

The retainer mechanism 56 for effecting withdrawal of the needle 25 selectively retains the needle 25 in the projecting configuration shown in FIGS. 1, 3 and 4. The releasable retainer mechanism 56 is formed to cooperate with the forward end 33 of the piston 15 to release the needle 25 in response to firm forceful movement of the piston 15. The retainer mechanism 56 will now be described with further reference to FIGS. 6–8.

The retainer mechanism 56 includes a plurality of latching projections or fingers 66 formed at the rear end 60 of the needle retainer 22. The fingers extend from the rearward portion of the needle retainer 22 into the interior of the ampoule housing 5. The fingers 66 are provided with substantially planar surfaces 67 integrally formed as part of fingers 66. The planar surfaces 67 extend in a direction which is substantially parallel to the longitudinal axis of needle 25. Further, the planar surfaces 67 are made to contact the outer surface of needle 25 to thereby maintain the needle 25 in proper orientation. Preferably, the planar surfaces 67 are secured or bonded to the outer surface of needle 25 using an adhesive or epoxy, such as one of the adhesives or epoxies listed in Table 1 hereinbelow.

TABLE 1

| Adhesive Type | Description | Supplier |
|---|---|---|
| Epoxy | EP30 | MasterBond |
| Epoxy | EP21LV | MasterBond |
| Epoxy | 301 RTC | Epoxy Technology |
| Epoxy | 353 RTC | Epoxy Technology |
| Epoxy | E32 | Permabond |
| Epoxy | C-7/A-34 | Armstrong |
| Epoxy | 3501 B/A Grey | Scotch-Weld |
| Epoxy | 3501 B/A Clear | Scotch-Weld |
| Epoxy | Henkel Versamid 125 catalyst/Shell Epon 828 resin | Henkel/Shell |
| Epoxy | Eccobond 1962-31 | W.R. Grace |
| Epoxy | Eccobond 927-10E | W.R. Grace |
| Epoxy | FDA-2 | Tracon |
| Epoxy | Eccobond LA 2843-23 | W.R. Grace |
| Cyanoacylate | 4011 | Loctite |
| Cyanoacylate | 4013 | Loctite |
| Cyanoacylate | 4161 | Loctite |
| UV cured adhesive | 3001 | Loctite |
| UV cured adhesive | 3011 | Loctite |
| UV cured adhesive | UV 9006 | W.R. Grace |
| UV cured adhesive | UV 9007 | W.R. Grace |
| UV cured adhesive | UV 9008 | W.R. Grace |

In the present preferred embodiment of the device, four fingers 66 are employed, but more or less fingers 66 may be employed depending on the size of the device, the nature of any biasing member (spring herein) and related structure in the device for effecting optimum operation.

The fingers 66 are bonded to the needle 25 to hold the needle 25 fixed in position in the needle retainer 22, and hence in the ampoule housing 5. The spring 29 surrounding the needle 25 is compressed within the needle retainer 22 and surrounds a rearward portion 27 of the needle 25. In the configuration of FIG. 8, the spring 29 is maintained in compression between the forward end of guideway 57 and the position 30 at which the spring 29 is attached to needle 25. An axial cavity or hollow area 61 is provided in the needle retaining mechanism 56 as well as in the front alignment member 55, which together define the needle retainer 22 in which the portion of the needle 25 and its surrounding spring 29 are positioned. Hence, the needle 25 is held in a biased relationship which urges the needle 25 toward the rear 17 of the ampoule 1, while being held by bonding to the retainer fingers.

The fingers 66 are preferably flexible to permit outward movement to break the bond and release the fingers 66 from the needle 25. It should also be appreciated that the fingers 66 could be fractured when moved outwardly to release the needle 25. The fingers 66 are formed to have rearward facing surfaces 62 canted or wedge-shaped for mating with the forward end 33 of the piston 15. When the fingers 66 are deformed or flexed radially outward by mating with the engaging surface of the piston 15 to release the fingers 66 from the needle 25, the expansive force of spring 29 immediately thrusts the needle 25 rearwardly toward the rear portion 17 of the ampoule 1.

The latching projections or fingers 66 with their planar surfaces 67 form a circular opening 63 at the rear end 60 of the needle retainer 22 for receiving the needle 25. The needle retainer 22 is provided with longitudinal grooves or score lines 64 running along the outside of the fingers 66 to facilitate breakage and separation of the fingers 66. The planar surfaces 67 of the fingers 66 preferably form a continuous axial surface within the interior of the needle retainer 22, to enhance the sealing characteristics of engagement with the needle 25. The continuous surfaces between the fingers 66 provide a seal with the needle 25, so that fluid is kept out of the chamber 11 in the ampoule apparatus 5. Additionally, a radially-protruding shoulder 68 may be formed around the exterior of the needle retainer 22 for abutment with a complementary ridge on the interior of the housing 5 to secure the needle retainer 22 against being pushed rearward by the expansive force of the compressed spring 29.

Referring to FIGS. 1 and 6, the piston 15 more specifically includes structural features for effecting release of the needle 25 from the needle retainer 22. The forward end 33 of the piston 15 has a cavity 34 at its center which is sealed by a frangible end plug 85 inserted centrally in cavity 34 at the forward end 33 of the piston 15. The frangible end member 85 is broken or separated from the piston 15 upon application of a force sufficient to separate the frangible end member 85 from the piston 15, when the frangible end plug 85 abuts against the rearward end 27 of the needle 25. The needle retainer 22 and the plunger 35 are preferably constructed to have the needle 25 provide suitable force for breaking the frangible end plug 85 prior to needle retraction. The piston 15 is chemically compatible with the stored medication. Polystyrene, for example, provides such characteristics for use with various medications. The properties of providing suitable frangibility for the frangible end plug 85 of the piston 15 and chemical compatibility may be provided separately by, for example, providing a conformal coating or layer of a chemically inert material, such as polytetrafluoroethylene, upon the surfaces of the piston 15 that is maintained in contact with the stored medication.

The periphery of the forward end 33 of the piston 15 is contoured or tapered to mate with and abut the cooperating wedge shaped surfaces 62 of the fingers 66 for spreading the fingers 66 to release the bond between the planar surfaces 67 of the fingers 66 and the needle 25. The forward progress of the piston 15 causes the fingers 66 to spread radially outward by flexing or breaking, thus releasing the needle 25. When the needle 25 is released from the needle retainer 22, the needle 25 is thrust rearwardly by the force of the compressed spring 29 and is propelled by the spring 29 through the aperture 69 in the forward end 33 of the piston 15, which had been closed by the frangible end member 85. The needle 25 is then received, and subsequently retained, within the cavity 37 in the plunger 35, as shown in FIG. 6.

A second embodiment of the present invention, characterized as a pre-filled injection ampoule 101 and ampoule holder 105, is shown in FIGS. 9–12. Similar parts in FIGS.

9–12 to those shown in FIGS. 1–8 are designated by the same reference numbers with the addition of 100 thereto.

The ampoule housing 105 of FIG. 9 differs from ampoule housing 5 of FIG. 1 primarily in that ampoule housing 105 has a cooperating needle guide 187, which receives the main needle 125 in a telescoping manner. The main needle 125 has its forward patient piercing portion 188 and its rearward portion 189 is sized to be slidingly received within the needle guide 187. In this arrangement, the length of the ampoule 101 and ampoule housing 105 in its as-shipped condition can be significantly reduced.

Figure 10:
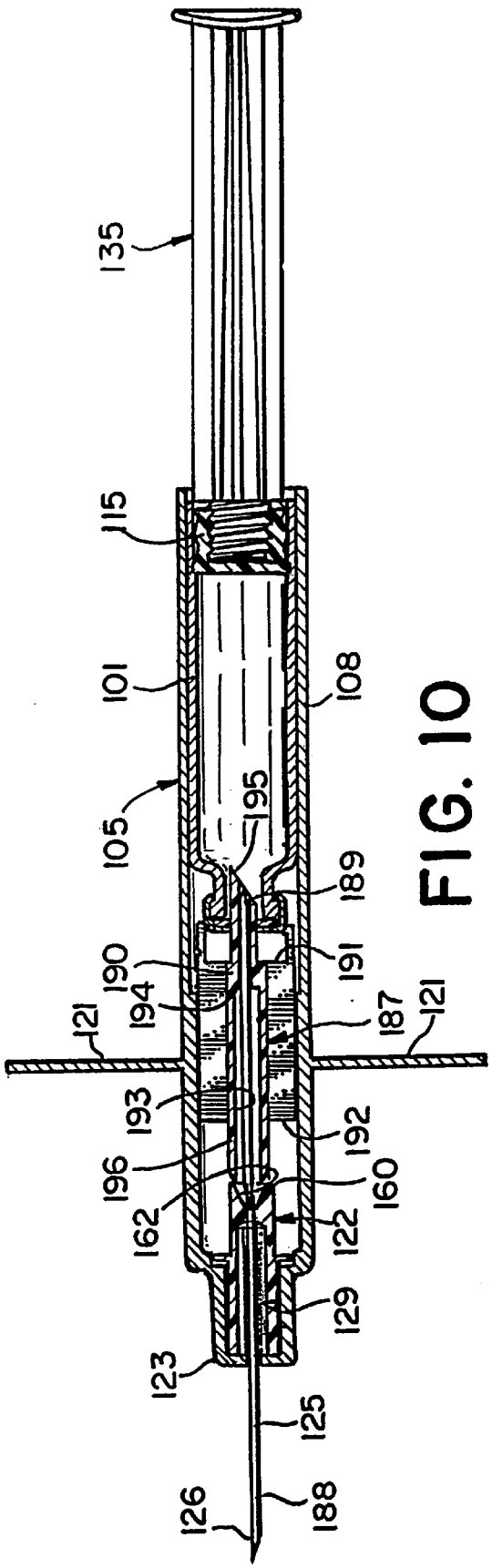
FIG. 10 is a cross-sectional view of the ampoule and ampoule apparatus of FIG. 9 showing the apparatus assembled prior to injection of fluid.
Figure 17A:
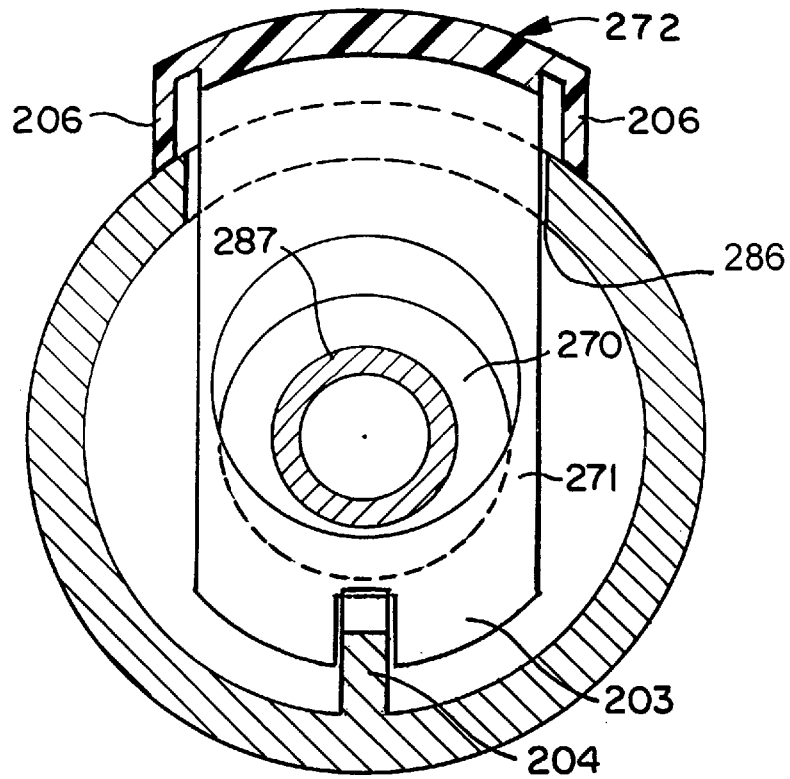
FIG. 17A is a cross-sectional view taken along line 17—17 of FIG. 16, showing the latch member in its locked position.
Figure 17B:
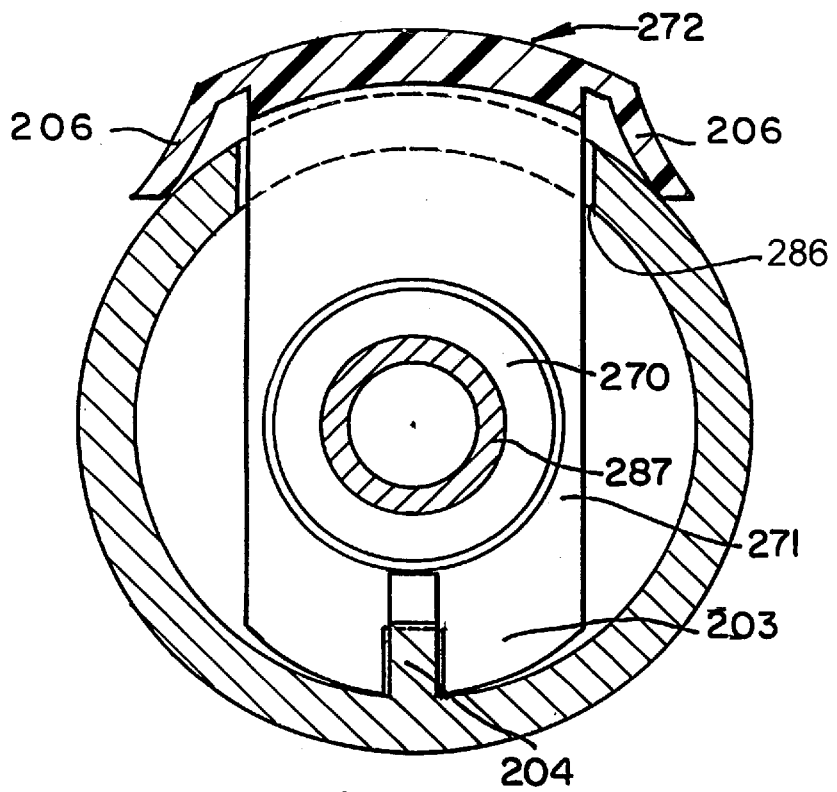
FIG. 17B is a cross-sectional view, similar to FIG. 17A, except the latch member is shown in its unlocked position.

As shown in FIG. 9, the needle guide 187 is generally cylindrical and is adapted to be slidably received within the barrel 108 of the ampoule housing 105. The needle guide 187 has a first axial bore 190 toward the rear end 191 of the needle guide 187. The diameter of the first axial bore 190 is selected to snugly receive the injection needle 125. The forward end 192 of the needle guide 187 has a second or enlarged axial bore 193, which communicates with the first axial bore 190. The diameter of the second axial bore 193 is sized to enable the injection needle 125 along with the attached spring 129 to be received within the second axial bore 193. When the needle retainer 122 is actuated for retraction of the injection needle 125, the compressed spring 129 propels the injection needle 125 rearwardly. The injection needle 188 and spring 129 thereby enter the second axial bore 193 and the transition 194 between the second axial bore 193 and the first axial bore 190 acts as a stop for the spring 129 and the needle 125 does not retract beyond passing into the ampoule 101, as shown in FIG. 12. The apparatus of FIG. 9 is shown in its shipping mode, and in FIG. 10 is shown assembled for use. FIG. 11 shows the apparatus after the medication is expelled from the ampoule 101. The piercing needle 125 is, as previously stated, shown retracted in FIG. 12, with the retraction being effected as described hereinbelow.

The radial clearance provided between the injection needle 125 and the first axial bore 190 in the needle guide 187 are selected to substantially prevent fluid leakage between the needle and guide 187 while an injection is given. These dimensional tolerances allow substantially all of the fluid initially contained within the ampoule 101 to be injected into a patient, with minimal retention of fluid within the injection device after an injection is given.

As best seen in FIG. 9, the needle guide 187 at its rearward end 191 has an outwardly, axially extending boss or piercing portion 189, which is beveled at its end to provide a piercing surface 195. The piercing surface 195 is adapted to penetrate the membrane 116 on the front end 113 of the ampoule 101 to have fluid injected from the ampoule 101 into the piercing portion 189 and hence the injection needle 125.

The forward end 192 of the needle guide 187 further includes a generally axially extending boss 196. The periphery of the boss 196 is contoured or tapered inwardly to mate with and abut the cooperating outwardly flared surfaces 162 of the fingers 166 for spreading the fingers 166 to brake the bond with the needle 125 to release the surfaces 167 from the needle 125. It should be appreciated that in this embodiment, the piston 115 in the ampoule need not have a contoured forward end 133, since it does not function to actuate the needle retainer 122.

In operation of the apparatus of FIGS. 9–12, the ampoule 101 is positioned within the barrel 108 of the ampoule housing 105 so that the forward end 113 of the ampoule 101 abuts, but is not punctured by, the rear end 197 of the piercing member 189. As shown in FIG. 9, the barrel 108 of ampoule housing 105 is sufficiently long to allow the ampoule 101 to be positioned within the interior of the barrel 108 of the housing 105. The plunger 135 is then detached from the forward end 123 of the housing 105 and attached to the piston 115. The ampoule 101 is then advanced within the barrel 108 of the ampoule housing 105 until the rear end 197 of the piercing member 189 punctures the membrane 116, which seals the forward end of the ampoule 101. The medication can then be administered in substantially the same manner as described in regard to FIGS. 1–6.

To retract the injection needle 125, pressure is applied to the plunger 135. The pressure advances the ampoule 101 forward to have the needle guide 187 pierce the piston 115 to open a conduit into the ampoule 101. At the same time, the periphery of the front boss 196 on the needle guide 187 presses against the needle retainer 122, thereby releasing the injection needle 125 for movement by the spring 129. The injection needle 125 and spring 129 are thus thrust rearwardly into the second axial bore 193 in the needle guide 187 for retraction of the injection needle 125 into the plunger 135 in the ampoule 101, as shown in FIG. 12.

A third embodiment of the present invention is shown in FIGS. 13–18. The third embodiment is the preferred embodiment and differs from the second embodiment primarily in that in the third embodiment, the ampoule 201 is evacuated without use of a plunger and the third embodiment has a different lock or latch mechanism 271 for preventing premature retraction of the needle 225. Similar parts in FIGS. 13–18 to those shown in FIGS. 9–12 are designated by the same reference number with the addition of 100 thereto.

The ampoule housing 205 of FIGS. 13–18 is similar to ampoule housing 105 of FIGS. 9–12. However, the needle guide 287 in the ampoule housing 205 of FIGS. 13–18 is snugly received in the interior of the housing 205, such as by a flange 299, which is held between detents 200 along the inner surface of the ampoule housing 205. Further, the rear end 291 of the needle guide 287 includes a piston adaptor, such as an axial extension member 280 having external threads. The axial extension member 280 is shaped to mate with the internal threads of an axial bore 246 in the piston 215, which seals one end of the ampoule 201. Further, a central bore 281 through the needle guide 287 allows the sharpened tip of the injection needle 288 to be retracted through the needle guide 287. Preferably, the first axial bore 246 of the needle guide 287 and the axially extending boss or piercing portion can be provided by a piercing needle 289, as shown in FIG. 16, which is adapted to receive the injection needle 288 in a telescoping arrangement, when the needle is retracted, as shown in FIG. 18.

In operation of the embodiment of FIGS. 13–18, the forward or piston end 213 of ampoule 201 is inserted within the barrel 208 of ampoule housing 205. The ampoule 201 is rotated to engage the threads on the needle guide 287 with the threaded cavity of the piston in the ampoule 201. When the needle guide 287 is fully engaged with the piston 215, the rear end 227 of the piercing needle 289 pierces through the piston 215 and into the interior cavity 282 of the ampoule 201, as shown in FIG. 14. Pressure is applied to the rear end 217 of the ampoule 201 to advance the ampoule 201 into the ampoule housing 205. As the ampoule 201 advances within the ampoule housing 205 with its piston 215 fixed in position, the medication is expelled from the cavity 282 in the ampoule 201 by the force of the piston 215 relative to the advancing ampoule 201. The ampoule 201 is advanced a sufficient distance to expel all of the medication from the ampoule 201. When all of the medication has been expelled, the piston 215 abuts the rear end 217 of the ampoule 201 and the forward end 213 of the ampoule 201 abuts the flange 299 of the needle guide 287. As shown in FIGS. 16, 17A and 17B, the needle guide 287 also has a forward flange or stop surface 270 that abuts a latch member 271, which extends into the ampoule housing 205 through a slot 286 in the sidewall. The latch member 271 is adapted to extend through the axial area of the ampoule 201 and be held by an abutment surface 204, which captures the latch member 271 and prevents the lower portion 203 of the latch member 271 from moving toward the front end 223 of the housing 205. When the flange or stop surface 270 of the needle guide 287 abuts the latch member 271, as shown in FIGS. 16 and 17A, the latch member 271 must be depressed toward the ampoule housing 205 to free the stop surface of the needle guide 287, as indicated in FIG. 17B, to allow further forward movement of the needle guide 287. The latch member 271 includes ears 206 to bias the latch member 271 to its locked position. When the latch member 271 is depressed, as shown in FIG. 17B, the ears 206 are deformed against their normal biasing condition to permit movement of the latch member 271 to its unlocked position, where it remains biased to its locked position by the ears 206. To retract the injection needle 225, further pressure is applied to the rear end 217 of the ampoule 201 to dislodge the flange 270 from the detent 200 along the inner surface of the ampoule housing 205, while the latch member 271 is depressed to its unlocked position. In this arrangement, the forward end 292 of the needle guide 287 is advanced to contact the needle retainer 222 causing the fingers 266 of needle retainer 222 to release the needle 225 by breaking the bond therebetween. The needle 225 is thereafter retracted, as shown in FIG. 18.

A fourth embodiment of the present invention is shown in FIGS. 19–23. The fourth embodiment is similar to the third embodiment, except that a plunger 335 is used to advance the piston 315 to expel the medication and activate retraction of the needle 325 in a manner similar to the structure of the embodiment of FIGS. 9–12, except that the lever lock 112 is replaced by latch member 271 of FIG. 16. Similar parts in FIGS. 19–23 to those shown in FIGS. 13–18 are designated by the same reference number with the addition of 100 thereto.

In the embodiment of FIGS. 19–23, the needle guide 387 includes a rear tubular member 383 and a forward tubular member 384. The rear tubular member 383 is beveled to pierce the membrane 316 on the forward end 313 of the ampoule 301. The forward tubular member 384 extends from the rear tubular member 383 and has a larger diameter than the rear tubular member 383. The diameter of the forward tubular member 384 is sized to enable the injection needle 388 along with the attached spring 329 to be received within the forward tubular member 384. The forward end 352 of the forward tubular member 384 is shaped to mate with and abut the outwardly beveled end 362 of the fingers 366 on the needle retainer 322 for moving the fingers 366 to break the bond to the needle 325 to effect retraction of the needle 325. The transition 394 between the forward and rearward tubular members 384 and 383 provides a stop for the spring 329, which is attached to the injection needle 388, as described relative to the embodiment of FIGS. 9 and 10. Fins 354 project radially from along the length of the forward and rearward tubular members 384 and 383 and contact the inner surface of the barrel 308 of the ampoule housing 305, thereby insuring that the tubular members 383 and 384 are properly aligned within the barrel 308 of the ampoule housing 305. The fins 354 also serve to properly align the needle guide 387 as it is advanced within the barrel 308 of the ampoule housing 305 to contact the fingers 366 of the needle retainer 322, as shown in FIG. 23.

In operation of the embodiment of FIGS. 19–23, the ampoule 301 is positioned within the barrel 308 of the ampoule housing 305 so that the forward end 313 of the ampoule 301 abuts, but is not punctured by, the rear end 397 of the piercing portion 389. The barrel 308 of ampoule housing 305 is sufficiently long to allow essentially the entire ampoule 301 to be positioned within the interior of the barrel 308 of housing 305. The plunger 335 is removed from over the injection needle 388 and is then attached to the piston 315. If provided with a sheath 328, the sheath 328 is removed from over the forward end 326 of the injection needle 388. The ampoule 301 is then advanced within the barrel 308 of the ampoule housing 305 until the rear end 397 of the piercing portion 389 punctures the membrane 316 which seals the forward end 313 of the ampoule 301, as shown in FIG. 20. The medication can then be administered in substantially the same manner as described above in regard to the embodiment of FIG. 9. FIG. 21 shows the apparatus after the medication has been expelled from the ampoule 301 into the patient.

To retract the injection needle 388, further pressure is applied to the plunger 335 and hence piston 315. The pressure on the piston 315 advances the ampoule 301 against the needle guide 387. The latch member 371 is then depressed to its unlocked position, as described in regard to the third embodiment. The ampoule 301 then presses against the fins 354 of the needle guide 387 to further advance the needle guide 387 to spread the fingers 366 of the needle retainer 322 to break the bond therebetween. More particularly, the forward end 352 of the forward tubular member 384 contacts the flared surfaces 367 of the fingers 366 on the needle retainer 322 releasing the injection needle 388. The injection needle 388 is retracted by force of the spring 329 and thrust rearwardly into the rearward tubular member 383. The injection needle 388 and spring 329 are prevented from passing through the rear tubular member 383 as previously described and shown in FIG. 23.

It should be appreciated that the method of needle retention between the needle and needle retainer by bonding, as well as the method of release of the needle retainer from the needle by breaking the bond, is applicable to a wide variety of medical devices beyond the ampoule devices described herein. More particularly, the needle holding and retraction arrangement could be used in syringes, phlebotomy devices and catheter insertion devices to effect holding and retraction of the needle which pierce patients. The retraction of the needle facilitates safety of medical personnel in disposing of such devices after use and prevents reuse of used devices.

Figure 27:
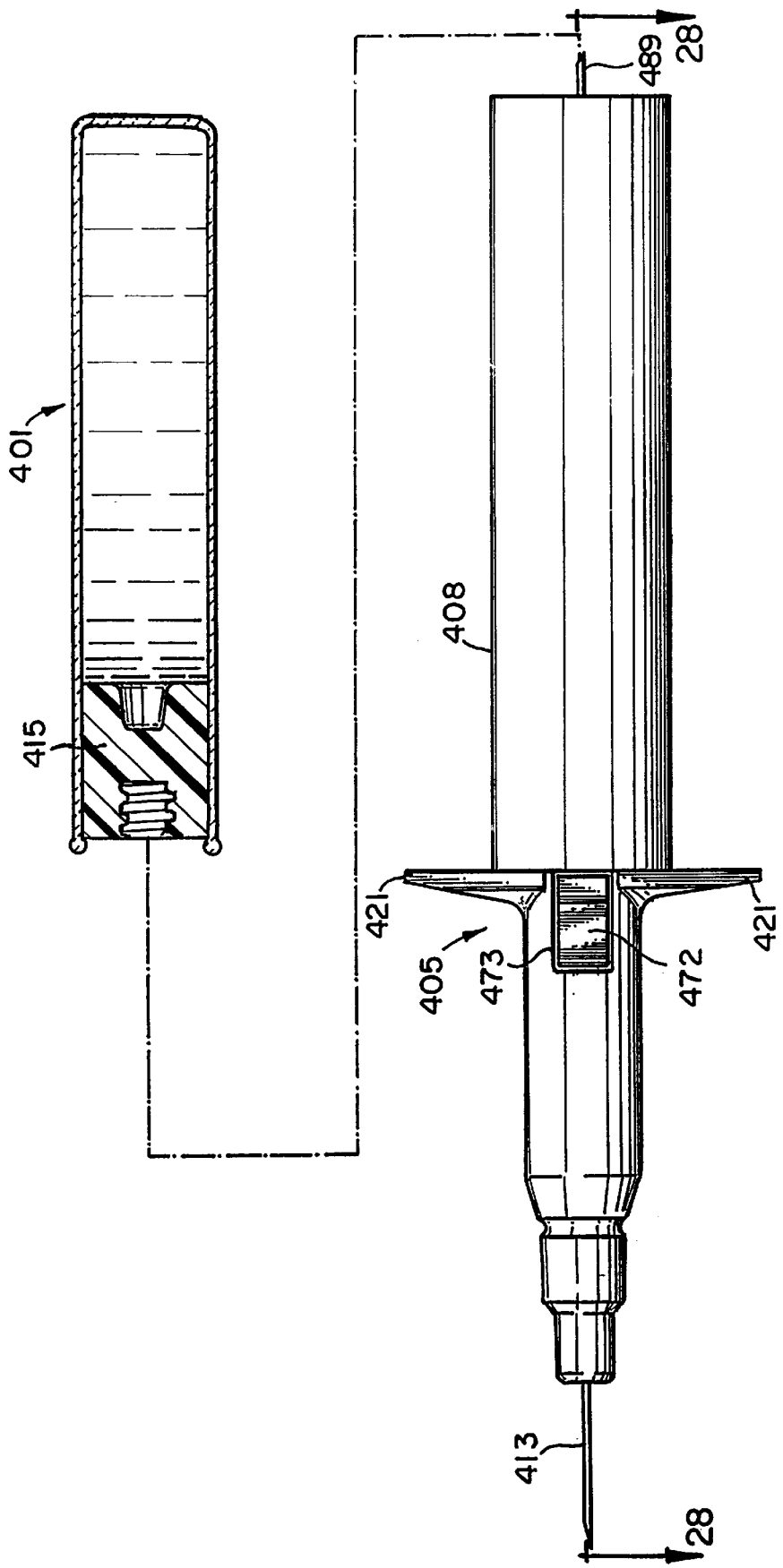
FIG. 27 is a side elevational view of a device for imparting fluid from a pre-filled cartridge, which is shown in cross section.

Referring now to FIG. 27, there is shown an injection device 405 for injecting fluid from a pre-filled vial or cartridge 401 into a patient through needle 413. The device 405 includes a barrel 408 sized to receive a cartridge 401 into the rear end of the barrel 408. The cartridge 401 contains a supply of fluid to be injected into a patient. The forward end of the cartridge 401 is sealed by a moveable piston or plug 415, which is puncturable by a rear needle 489 positioned axially within the barrel 408. A pair of finger grips 421 are formed to extend outwardly from the barrel 408 to allow a user to stabilize the device 405 while an injection is administered.

In order to prevent undesired premature retraction of the needle 413, the device 405 includes a safety latch having a button or other actuating surface 472 protruding outwardly through an opening 473 formed in the barrel 408. When an injection is administered, the cartridge 401 is advanced into the rear of the barrel 408, thus puncturing the plug 415 with the rear needle 489. Further advancement of the cartridge 401 drives the catridge over the plug 415 to expel fluid through the needle 413.

Figure 28:
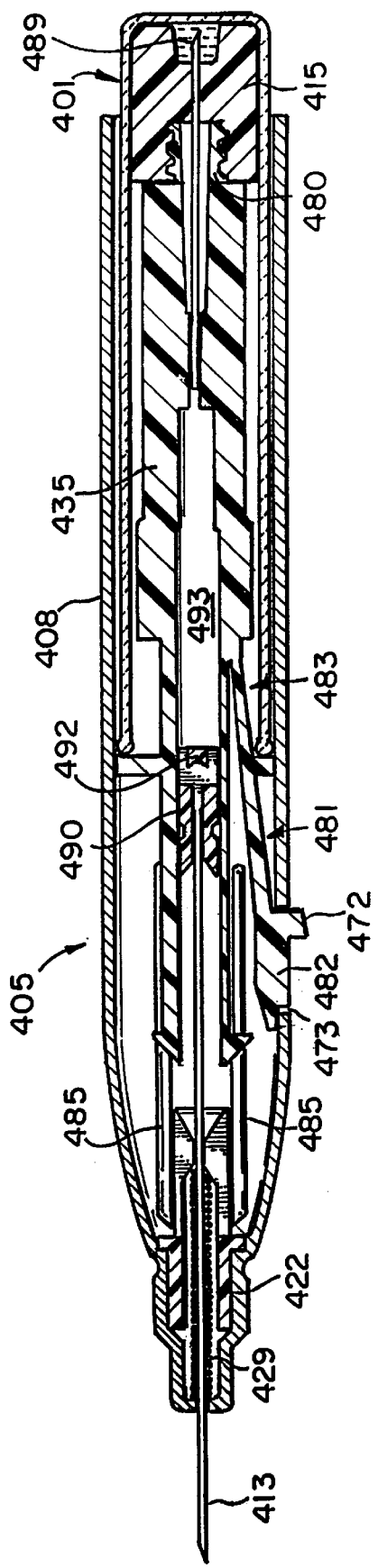
FIG. 28 is a sectional view of the device of FIG. 27 taken along the line 27–28 thereof, with the cartridge inserted therein.

At the end of an injection stroke, the device 405 and the cartridge 401 are configured as shown in FIG. 28. When the cartridge 401 is driven over the plug 415, the rear end of the stationary piston 435 maintains the plug stationary relative to the cartridge. The cartridge 401 is driven over the plug 415 until the plug abuts the rear of the cartridge. The stationary piston 435 is axially positioned in the barrel 408, and has a threaded boss 480 formed at the rear end thereof for engagement with the plug 415. The piston 435 has an axial cavity 493 formed therein having a reduced diameter rear portion for supporting the rear needle 489 and for conducting fluid from the vial to the forward needle 413 during an injection.

The forward needle 413 extends in a projecting configuration from the forward end of the barrel 408. The needle 413 is surrounded by a compressed spring 429 within the forward interior portion of the barrel 408, the rear portion of the spring 429 is bonded to the needle 413 or otherwise arranged to exert a rearward bias upon the needle 413. The needle 413 is maintained in the projecting configuration by engagement with a needle retainer 422 substantially of the type described hereinabove. The forward end of the plunger 435 is configured for releasing the engagement between the needle 413 and the needle retainer 422.

After the end of an injection stroke, actuation of the plunger 435 to release the needle 413 is prevented by a latch 481 extending outwardly from the plunger 435. The latch 481 has a releasable detent 482 formed thereon for abutment with the rim of an opening 473 formed in the barrel 408. The latch 481 further includes a flexible cantilever beam 483 connected with the plunger 415. The beam 483 biases the detent 482 to extend through the opening 473 during use of the device 405. When inward pressure is exerted against actuating surface 472 of the detent 482, the beam 483 deflects inwardly to permit the detent 482 to be moved out of abutment with the rim of opening 473. Then, while such pressure is maintained against surface 472, the user may urge cartridge 401 further into the barrel 408 to move the piston 435 in the forward direction, and thus to effect needle retraction. Centering means, such as ribs 485 formed on the interior of the barrel 408, are provided to maintain axial alignment between the forward end of the plunger 415 and the rear of the needle retainer 422.

The device 405 preferably incorporates means for preventing residual fluid from undesirable being ejected from the needle 413 during retraction. In the embodiment shown in FIG. 28, the rear portion of needle 413 extends into the forward portion of the axial cavity 493 of the plunger 413. A plug support member 490 is positioned in the cavity 493 to hold a plug 492 in axial alignment with the rear end of the needle. When the needle is to be retracted, the plug support member 490, and hence the plug 492, are moved forward with the plunger 435 to allow the plug 492 to contact and seal the rear end of the needle 413. As the plunger is moved forward, the needle retainer 422 is released from the needle, and the plug 492 separates from the plug support member 490 in order to remain on the rear of the end the needle 413 to provide a partial vacuum in the rear portion of rearwardly-excelerating needle 413. Thus, residual fluid is retained in the needle 413.

Figure 29:
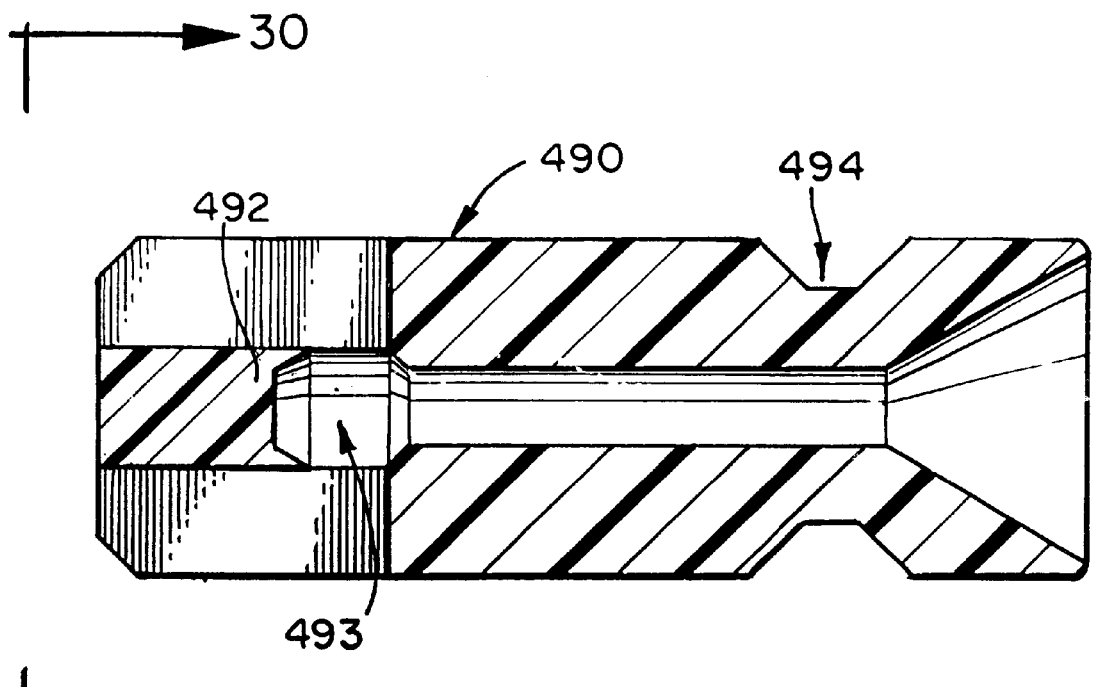
FIG. 29 is a sectional view of a plug support member for providing an anti-fluid ejection mechanism for the device of FIG. 27.
Figure 30:
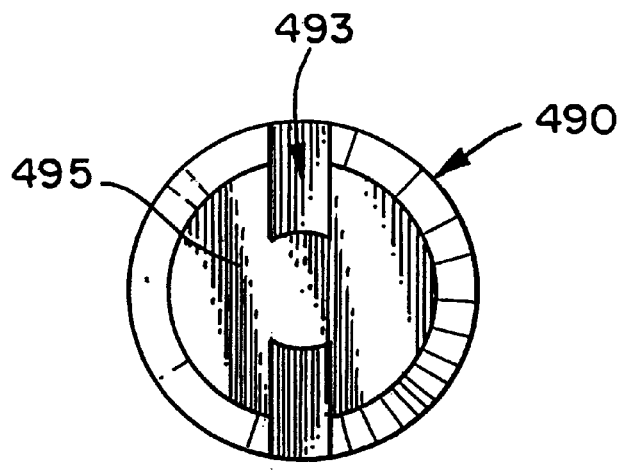
FIG. 30 is a rear elevational view of the plug support member of FIG. 29.

Referring now to FIG. 29, the plug 492 and the plug support member 490 are preferably integrally formed of an elastomeric material. The plug support member 490 preferably has a waist 494 formed about its exterior for engaging a complementary interior surface of the plunger 435. Additionally, the plug support member has an axial cavity formed therein for receiving and holding the rear portion of the forward needle 413 during assembly of the device 405. As can be seen in FIG. 30, the plug 492 is supported to align with the rear end of the needle by a web 495, which forms the rear portion of the plug support member 490. The web 495 includes opening 493 formed therein to provide a fluid flow path through the rear portion of the plug support member 490 contiguous with the central cavity thereof. When the plunger is actuated to effect needle retraction, the forward end of the plug is driven onto the rear end of the needle. The waist 494 provides sufficient retention force for the plug support member 490 within the plunger 435 such that further forward motion of the plunger breaks the web 495, and hence allows plug 492 to remain on the rear end of the needle as it retracts.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention.

That which is claimed is:

1. A medical device operable in connection with a fluid container having a pierceable member, comprising:
    a hollow housing comprising a socket configured to receive the fluid container;
    a first needle having a sharpened tip operable in a projecting position in which the sharpened tip projects forwardly from the housing and a retracted position in which the sharpened tip is retracted into the housing;
    a second needle projecting into the socket for piercing the pierceable member;
    a needle retainer releasably retaining the needle in the projecting position, the needle retainer having a rearwardly facing actuation surface;
    a plunger slidably displaceable within the housing, the plunger having a front portion cooperable with the actuation surface of the needle retainer; and
    a latch manually operable between a latched position in which the latch impedes forward axial motion of the plunger, and an unlocked position in which the plunger can be displaced axially forwardly;
    wherein operation of the latch and the plunger releases the first needle from the needle retainer so that the first needle can be retracted into the housing.

2. The device of claim 1 wherein simultaneous operation of the latch and the plunger releases the first needle from the needle retainer so that the first needle can be retracted into the housing.

3. The device of claim 1, comprising a spring connected to the first needle, biasing the first needle rearwardly into the housing.

4. The device of claim 1 wherein the plunger comprises a chamber for receiving the first needle in the retracted position.

5. The device of claim 1 wherein the needle retainer comprises a plurality of longitudinally-elongated circumferentially-spaced fingers projecting inwardly to retain the needle.

6. The device of claim 1 wherein the plunger comprises a fluid receiving cavity.

7. The device of claim 3 comprising a spring chamber for receiving the spring, wherein the needle retainer forms the rearward end of the spring chamber.

8. The device of claim 1 wherein the latch comprises an actuation portion external of the housing.

9. A medical device, comprising:

a hollow housing;

a needle projecting forwardly from the housing;

a needle retainer releasably retaining the needle projecting forwardly from the housing;

a first actuator operable in a first direction and being cooperable with the needle retainer to release the needle; and a second actuator for impeding operation of the first actuator, wherein the second actuator is operable in a direction transverse the first direction and simultaneous operation of the first actuator and the second actuator releases the needle so that the needle can be retracted into the housing.

10. The device of claim 9 wherein the housing comprises a socket configured to receive a fluid container having a pierceable member.

11. The device of claim 10 comprising a second needle in fluid communication with the first needle, wherein the second needle projects into the socket for piercing the pierceable member.

12. The device of claim 9 wherein the second actuator is a latch having an actuating surface projecting externally from the housing.

13. The device of claim 9 wherein the needle retainer comprises a plurality of longitudinally-elongated circumferentially-spaced fingers projecting inwardly to retain the needle.

14. The device of claim 9 comprising a spring connected to the needle, biasing the needle rearwardly into the housing.

15. The device of claim 9 wherein the first actuator comprises a chamber for receiving the needle.

16. The device of claim 9 wherein the needle retainer comprises a rearwardly facing actuation surface and the first actuator comprises a forward portion configured to cooperate with the actuation surface, so that upon forward displacement of the first actuator, the front portion engages the actuation surface, radially deforming the actuation surface, thereby releasing the needle from the needle retainer.

17. A medical device, comprising:

a hollow housing;

a needle having a sharpened tip operable in a projection position, in which the sharpened tip of the needle projects forwardly from the barrel and a retract position in which the sharpened tip of the needle is enclosed within the housing;

a biasing element biasing the needle toward the retracted position;

a needle retainer releasably retaining the needle in the projecting position;

a first actuator cooperable with the needle retainer to release the needle to allow the biasing element to displace the needle into the retracted position; and a second actuator for impeding operation of the first actuator, extending radially outwardly, transverse the first actuator.

18. The device of claim 17 wherein the second actuator is radially deformable.

19. The device of claim 17 wherein the housing is configured to receive a fluid container having a pierceable membrane.

20. The device of claim 17 wherein simultaneous operation of the first actuator and the second actuator releases the needle so that the needle can be retracted into the housing.

* * * * *